US008217120B2

(12) United States Patent
Dershem

(10) Patent No.: US 8,217,120 B2
(45) Date of Patent: Jul. 10, 2012

(54) FUNCTIONALIZED STYRENE OLIGOMERS AND POLYMERS

(75) Inventor: Stephen M. Dershem, San Diego, CA (US)

(73) Assignee: Designer Molecules, Inc., San Diego, CA (US)

(*) Notice: Subject to any disclaimer, the term of this patent is extended or adjusted under 35 U.S.C. 154(b) by 209 days.

(21) Appl. No.: 12/540,892

(22) Filed: Aug. 13, 2009

(65) Prior Publication Data

US 2010/0041832 A1 Feb. 18, 2010

Related U.S. Application Data

(60) Provisional application No. 61/088,617, filed on Aug. 13, 2008.

(51) Int. Cl.
C08L 37/00 (2006.01)
C08L 25/02 (2006.01)
C08F 255/00 (2006.01)
C08C 19/22 (2006.01)
C08C 19/00 (2006.01)

(52) U.S. Cl. ........ 525/208; 525/241; 525/302; 525/319; 525/375; 525/385

(58) Field of Classification Search .................. 525/208, 525/241, 302, 319, 375, 385
See application file for complete search history.

(56) References Cited

U.S. PATENT DOCUMENTS

| | | | |
|---|---|---|---|
| 3,905,820 A | 9/1975 | Frass | |
| 4,111,879 A | 9/1978 | Mori et al. | |
| 4,540,829 A | 9/1985 | Hefner | |
| 4,968,738 A | 11/1990 | Dershem | |
| 4,994,989 A | 2/1991 | Usami et al. | |
| 5,045,127 A | 9/1991 | Dershem et al. | |
| 5,064,480 A | 11/1991 | Dershem et al. | |
| 5,155,177 A | 10/1992 | Frihart | |
| 5,232,962 A | 8/1993 | Dershem et al. | |
| 5,266,610 A | 11/1993 | Malhotra et al. | |
| 5,306,333 A | 4/1994 | Dershem et al. | |
| 5,358,992 A | 10/1994 | Dershem et al. | |
| 5,403,389 A | 4/1995 | Dershem | |
| 5,430,112 A | 7/1995 | Sakata et al. | |
| 5,447,988 A | 9/1995 | Dershem et al. | |
| 5,489,641 A | 2/1996 | Dershem | |
| 5,567,761 A | 10/1996 | Song | |
| 5,602,205 A | 2/1997 | Singh et al. | |
| 5,646,241 A | 7/1997 | Dershem et al. | |
| 5,714,086 A | 2/1998 | Osuna et al. | |
| 5,717,034 A | 2/1998 | Dershem et al. | |
| 5,718,941 A | 2/1998 | Dershem et al. | |
| 5,753,748 A | 5/1998 | Dershem et al. | |
| 5,760,165 A | 6/1998 | Dao et al. | |
| 5,861,111 A | 1/1999 | Dershem et al. | |
| 5,969,036 A | 10/1999 | Dershem | |
| 5,973,166 A | 10/1999 | Mizori et al. | |
| 6,034,150 A | 3/2000 | Hoyle et al. | |
| 6,034,194 A | 3/2000 | Dershem | |
| 6,034,195 A | 3/2000 | Dershem | |
| 6,048,953 A | 4/2000 | Kawashimu et al. | |
| 6,121,358 A | 9/2000 | Dershem et al. | |
| 6,187,886 B1 | 2/2001 | Husson et al. | |
| 6,211,320 B1 | 4/2001 | Dershem et al. | |
| 6,300,456 B1 | 10/2001 | Musa | |
| 6,355,750 B1 | 3/2002 | Herr | |
| 6,369,124 B1 | 4/2002 | Hoyle et al. | |
| 6,423,780 B1 | 7/2002 | Dershem et al. | |
| 6,429,281 B1 | 8/2002 | Dershem et al. | |
| 6,521,731 B2 | 2/2003 | Dershem et al. | |
| 6,620,946 B2 | 9/2003 | Dershem et al. | |
| 6,743,852 B2 | 6/2004 | Dershem et al. | |
| 6,750,301 B1 | 6/2004 | Bonneau et al. | |
| 6,790,597 B2 | 9/2004 | Dershem | |
| 6,825,245 B2 | 11/2004 | Dershem | |

(Continued)

FOREIGN PATENT DOCUMENTS

CN 1187507 A 7/1998

(Continued)

OTHER PUBLICATIONS

Adamson, "Review of CSP and Flip Chip Underfill Processes and When to Use the Right Dispensing Tools for Efficient Manufacturing", Paper Presented at GlobalTRONICS Technology Conference,Singapore 2002, 1-6.

Anand et al., "Copolymerization and thermal behavior of methyl methacrylate with N-(phenyl/p-tolyl) itaconimides", Journal of Applied Polymer Science 89: 2003, 1195-1202.

Andersson et al., "Initiator-Free Photopolymerization of an Aliphatic Vinyl Ether-Maleimide Monomer", J Coatings Tech 69 1997, 91-95.

DSM, "Hybrane (TM) DSM's new dendritic polymers", DSM New Business Development product literature 99-1c: 1999, 1-10.

Grenier-Loustalot, et al., "Monofunctional maleimide or acetylene terminated model compounds-I. Molten state homopolymerization reactivity and kinetics", European Polymer Journal 34: 1998, 1705-1714.

Klang, "Radiation-curable Hyperbranched Polyester Acrylates", PCI Magazine Apr. 2007, 98-101.

Kohli, et al., "Co-Polymerization of Maleimides and Vinyl Ethers: A Structural Study", Macromolecules 31: 1998, 5681-5689.

Yamazaki, et al., "Effect of N-substrtuents on polymerization reactivity of N-alkylitaconimides in radical polymerization", European Polymer Journal 33: 1997, 157-162.

(Continued)

Primary Examiner — William Cheung
(74) Attorney, Agent, or Firm — The Law Office of Jane K. Babin, Professional Corporation; Jane K. Babin

(57) ABSTRACT

The present invention provides functionalized styrene oligomers and polymers prepared by Friedel-Crafts chemistry, as well as epoxidation products thereof. In particular, the invention provides allyl functional TPE. The invention also provides methods for making the functionalized styrene oligomers and polymers of the invention as well as epoxidation products thereof, compositions containing the same, and methods for using the functionalized and epoxified styrene oligomers that take advantage of the unique properties of the compounds and compositions of the invention.

16 Claims, No Drawings

U.S. PATENT DOCUMENTS

| | | |
|---|---|---|
| 6,831,132 B2 | 12/2004 | Liu et al. |
| 6,852,814 B2 | 2/2005 | Dershem et al. |
| 6,855,745 B2 | 2/2005 | Hoyle et al. |
| 6,916,856 B2 | 7/2005 | Dershem |
| 6,946,523 B2 | 9/2005 | Dershem et al. |
| 6,960,636 B2 | 11/2005 | Dershem et al. |
| 6,963,001 B2 | 11/2005 | Dershem et al. |
| 7,102,015 B2 | 9/2006 | Dershem et al. |
| 7,157,587 B2 | 1/2007 | Mizori et al. |
| 7,176,044 B2 | 2/2007 | Forray et al. |
| 7,199,249 B2 | 4/2007 | Liu et al. |
| 7,208,566 B2 | 4/2007 | Mizori et al. |
| 7,285,613 B2 | 10/2007 | Dershem et al. |
| 7,309,724 B2 | 12/2007 | Dershem et al. |
| 7,326,754 B2 | 2/2008 | Nikolic et al. |
| 7,517,925 B2 | 4/2009 | Dershem et al. |
| 7,678,879 B2 | 3/2010 | Dershem |
| 2002/0062923 A1 | 5/2002 | Forray |
| 2002/0099168 A1 | 7/2002 | Dershem et al. |
| 2002/0188137 A1 | 12/2002 | Dershem et al. |
| 2002/0193541 A1 | 12/2002 | Dershem et al. |
| 2002/0198356 A1 | 12/2002 | Dershem et al. |
| 2003/0008992 A1 | 1/2003 | Dershem et al. |
| 2003/0055121 A1 | 3/2003 | Dershem et al. |
| 2003/0060531 A1 | 3/2003 | Dershem et al. |
| 2003/0083436 A1 | 5/2003 | Deitch |
| 2003/0087999 A1 | 5/2003 | Dershem et al. |
| 2003/0109666 A1 | 6/2003 | Dershem et al. |
| 2003/0125551 A1 | 7/2003 | Dershem et al. |
| 2003/0199638 A1 | 10/2003 | Liu et al. |
| 2003/0208016 A1 | 11/2003 | Dershem et al. |
| 2004/0006166 A1 | 1/2004 | Liu et al. |
| 2004/0019224 A1 | 1/2004 | Dershem et al. |
| 2004/0077798 A1 | 4/2004 | Dershem et al. |
| 2004/0082724 A1 | 4/2004 | Dershem et al. |
| 2004/0102566 A1 | 5/2004 | Forray et al. |
| 2004/0123948 A1 | 7/2004 | Dershem et al. |
| 2004/0225026 A1 | 11/2004 | Mizori et al. |
| 2004/0225045 A1 | 11/2004 | Forray |
| 2004/0225059 A1 | 11/2004 | Mizori et al. |
| 2005/0027082 A1 | 2/2005 | Narayan-Sarathy et al. |
| 2005/0107542 A1 | 5/2005 | Liu et al. |
| 2005/0136620 A1 | 6/2005 | Dershem et al. |
| 2005/0137277 A1 | 6/2005 | Dershem et al. |
| 2005/0137340 A1 | 6/2005 | Nikolic et al. |
| 2005/0267254 A1 | 12/2005 | Mizori et al. |
| 2005/0272888 A1 | 12/2005 | Dershem et al. |
| 2006/0009570 A1 | 1/2006 | Zychowski |
| 2006/0009578 A1 | 1/2006 | Dershem |
| 2006/0030672 A1 | 2/2006 | Nikolic et al. |
| 2006/0063014 A1 | 3/2006 | Forray |
| 2006/0069232 A1 | 3/2006 | Dershem |
| 2006/0116476 A1 | 6/2006 | Cheng |
| 2006/0142517 A1 | 6/2006 | Dershem |
| 2007/0155869 A1 | 7/2007 | Dershem et al. |
| 2007/0205399 A1 | 9/2007 | Mizori |
| 2007/0299154 A1 | 12/2007 | Dershem et al. |
| 2008/0017308 A1 | 1/2008 | Dershem et al. |
| 2008/0075961 A1 | 3/2008 | Mizori |
| 2008/0075963 A1 | 3/2008 | Dershem |
| 2008/0075965 A1 | 3/2008 | Dershem |
| 2008/0103240 A1 | 5/2008 | Dershem |
| 2008/0142158 A1 | 6/2008 | Dershem |
| 2008/0146738 A1 | 6/2008 | Dershem |
| 2008/0160315 A1 | 7/2008 | Forray et al. |
| 2008/0191173 A1 | 8/2008 | Dershem et al. |
| 2008/0210375 A1 | 9/2008 | Dershem et al. |
| 2008/0251935 A1 | 10/2008 | Dersham |
| 2008/0257493 A1 | 10/2008 | Dershem |
| 2008/0262191 A1 | 10/2008 | Mizori |
| 2009/0061244 A1 | 3/2009 | Dershem |
| 2009/0215940 A1 | 8/2009 | Dershem |
| 2009/0288768 A1 | 11/2009 | Dershem |
| 2010/0041803 A1 | 2/2010 | Dershem |
| 2010/0041823 A1 | 2/2010 | Dershem |
| 2010/0041845 A1 | 2/2010 | Dershem et al. |
| 2010/0056671 A1 | 3/2010 | Dershem |
| 2010/0063184 A1 | 3/2010 | Dershem |

FOREIGN PATENT DOCUMENTS

| | | | |
|---|---|---|---|
| EP | 0393713 | | 6/1994 |
| EP | 1156034 | | 11/2001 |
| EP | 1156036 | | 11/2001 |
| EP | 1834969 | | 9/2007 |
| JP | 10287715 | | 10/1998 |
| JP | 2003002919 | | 1/2003 |
| WO | WO-9406862 | | 3/1994 |
| WO | WO-2005121190 | | 12/2005 |
| WO | WO-2007100329 | | 9/2007 |
| WO | WO 2008/077141 | * | 6/2008 |
| WO | WO-2008077141 | | 6/2008 |
| WO | WO-2008124797 | | 10/2008 |
| WO | WO-2008130894 | | 10/2008 |
| WO | WO-2010019832 | | 2/2010 |

OTHER PUBLICATIONS

* cited by examiner

FUNCTIONALIZED STYRENE OLIGOMERS AND POLYMERS

RELATED APPLICATIONS

This application claims the benefit of priority under 35 USC §119 of U.S. Provisional Applications Ser. No. 61/088,617 filed Aug. 13, 2009, the entire disclosure of which is incorporated herein by reference.

FIELD OF THE INVENTION

The present invention relates to functionalized styrene-containing compounds compositions, methods of preparation and uses therefor. In particular, the present invention relates to functionalized styrene oligomers and polymers prepared by Friedel-Crafts chemistry and epoxidation products thereof. Specific compounds of the invention include functionalized styrene-containing thermoplastic elastomers

BACKGROUND OF THE INVENTION

As the electronics industry advances, and production of light weight components increases, the development of new materials gives producers increased options for further improving the performance and ease of manufacture of such components. Adhesive compositions are used for a variety of purposes in the fabrication and assembly of semiconductor packages and microelectronic devices. The more prominent uses include bonding of electronic elements such as integrated circuit (IC) chips to lead frames or other substrates, and bonding IC chips to other IC chips. Adhesives useful for electronic packaging applications typically exhibit properties such as good mechanical strength, curing properties that do not affect the component or the carrier, and rheological properties compatible with application to microelectronic and semiconductor components.

The demand for smaller and more powerful electronic components presents certain challenges to the microelectronic packaging industry. One way to include more semiconductor die in a component without increasing circuit board area is to arrange the die in a stacked configuration. Indeed, "stacked die" packages conserve "circuit board real estate" without sacrificing power or performance of the electronic component. In addition, the die used in stacked die applications are becoming ever thinner, requiring new adhesive solutions in order to preserve the integrity of these very thin die.

Moreover, other configurations of computer chips on circuit board such as those that require direct attachment to a substrate or board (e.g. "Flip Chips"), required similar properties to achieve higher speed and chip density on circuit boards. Yet with high density and direct contact between circuit boards and chips, there is concern about the thermo-mechanical expansion mismatch between the chip and the substrate or board, as well as concern that moisture can cause problems with tiny solder joints.

Thus, the microelectronics industry continues to require new adhesives that are able to meet its varying demands. Accordingly, there is a need for the development of materials to address the requirements of this rapidly evolving industry.

SUMMARY OF THE INVENTION

The present invention provides functionalized styrene oligomers and polymers prepared by Friedel-Crafts chemistry as well as epoxidation products thereof. In certain embodiments, the compounds of the invention have the structure of formula I:

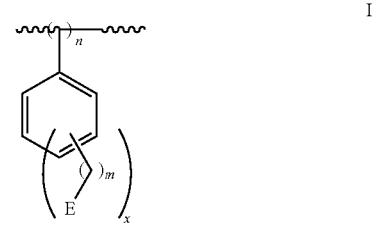

where E is a moiety selected from the group consisting of maleimido, acrylate, methacrylate, allyl, methallyl, epoxy, oxetane, a partially or fully epoxidized allyl, a partially or fully epoxidized methallyl; n is an integer having the value between 3 and about 100; m is an integer having the value between 0 and 12; and x is an integer having the value between 1 and 5. In certain aspects of the invention, E is selected from allyl, methallyl, epoxy, acrylate, and methacrylate. In other embodiments, E is allyl, partially or fully epoxidized allyl, methallyl and partially or fully epoxidized methallyl.

Exemplary compounds of the invention include Compounds 1-6:

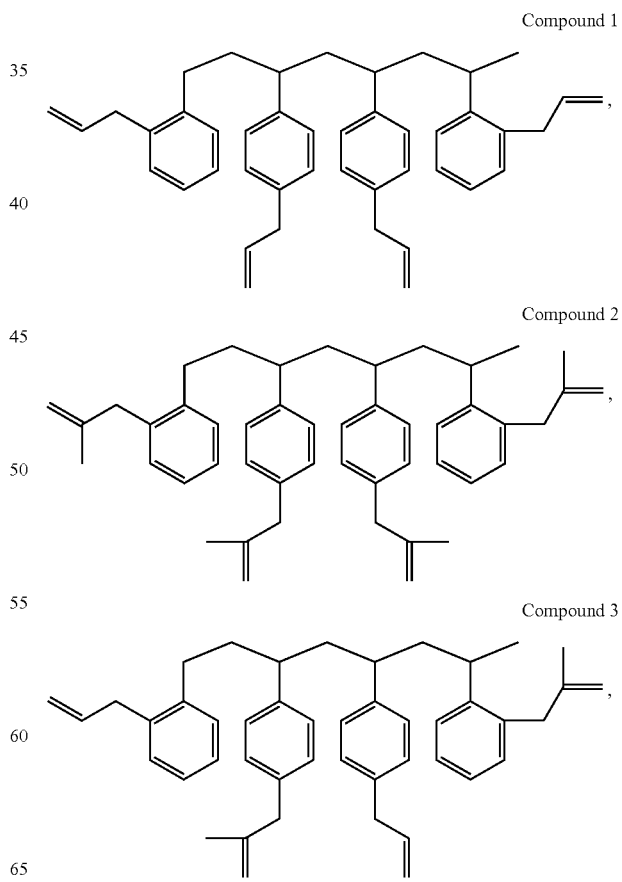

Compound 4

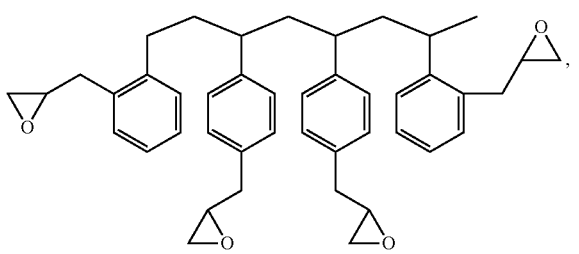

Compound 5

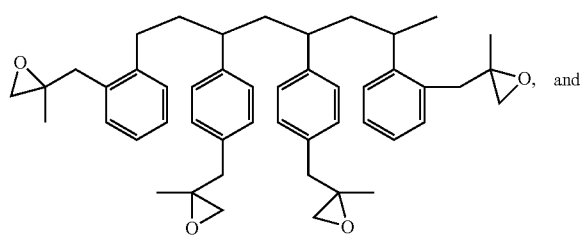, and

Compound 6

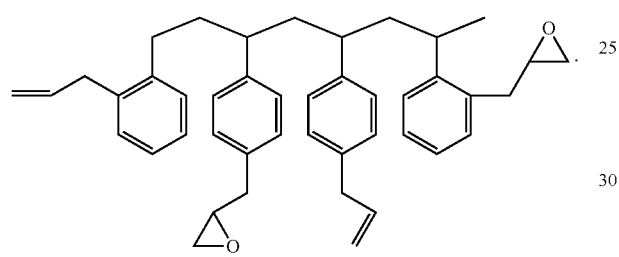

The present invention also provides block copolymers having the structure represented by formula II or III:

$$(A-B)_y \quad \text{II}$$
$$(A-B)_y-A \quad \text{III}$$

where each A is a compound of according to formula I, wherein E is a moiety selected from the group consisting of maleimido, acrylate, methacrylate, allyl, methallyl, epoxy, and oxetane; each B is a hydrogenated polybutadiene polymer; and y is an integer having the value between 1 and about 100.

Also provided are block copolymers having the structure represented by formula IV or V:

$$(A'-B)_y \quad \text{IV}$$
$$(A'-B)_y-A \quad \text{V}$$

where each A' is a compound according to formula I, wherein E is a moiety selected from the group consisting of a partially or fully epoxidized allyl, and a partially or fully epoxidized methallyl; each B is a hydrogenated polybutadiene polymer; and y is an integer having the value between 1 and about 100.

The invention also provides compositions containing a compound according to formula I. Such compositions may be, for example, adhesive compositions. Adhesive compositions of the invention may be cured or uncured. In certain embodiments, the adhesive composition is B-stageable. In various aspects of the invention, compositions may include at least one curing initiator, co-monomer, co-curing compound, coupling agent, or filler. Compositions including block polymers according to the invention, including adhesive compositions, are also provided.

The present invention also provides methods for increasing the adhesiveness of a composition comprising a monomer, by replacing all or a portion of the monomer in the composition with a compound of formula I. The monomer can be, for example, a bismaleimide or an acrylate. In certain embodiments, replacing all or a portion of the monomer in the composition increases the adhesiveness of the composition by at least about 100%.

In yet further embodiments of the invention, methods for functionalizing a styrene oligomer or polymer are provided, which include the step of alkylating a styrene oligomer or polymer according to the reaction Scheme A:

Scheme A

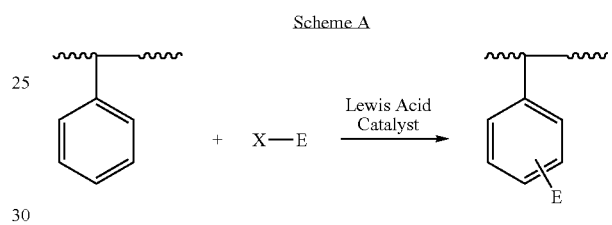

where E is selected from the group consisting of maleimido, acrylate, methacrylate, allyl, methallyl, epoxy, and oxetane, thereby obtaining a functionalized styrene oligomer or polymer. In certain aspects of this method, E is allyl or methallyl and X is Cl, Br, I, —OH, or α-olefin. In yet other embodiments, the method further includes the step of partially or fully oxidizing the allyl or methallyl functional groups to epoxy residues. The present invention also provides oligomers and polymers obtained by the methods of the invention.

DETAILED DESCRIPTION

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting. The section headings used herein are for organizational purposes only and are not to be construed as limiting the subject matter described.

Unless specific definitions are provided, the nomenclatures utilized in connection with, and the laboratory procedures and techniques of analytical chemistry, synthetic organic and inorganic chemistry described herein are those known in the art, such as those set forth in "IUPAC Compendium of Chemical Terminology: IUPAC Recommendations (The Gold Book)" (McNaught ed.; International Union of Pure and Applied Chemistry, 2nd Ed., 1997) and "Compendium of Polymer Terminology and Nomenclature: IUPAC Recommendations 2008" (Jones et al., eds; International Union of Pure and Applied Chemistry, 2009). Standard chemical symbols are used interchangeably with the full names represented by such symbols. Thus, for example, the terms "hydrogen"

and "H" are understood to have identical meaning. Standard techniques may be used for chemical syntheses, chemical analyses, and formulation.

Definitions

"About" as used herein means that a number referred to as "about" comprises the recited number plus or minus 1-10% of that recited number. For example, "about" 100 degrees can mean 95-105 degrees or as few as 99-101 degrees depending on the situation. Whenever it appears herein, a numerical range such as "1 to 20" refers to each integer in the given range; e.g., "1 to 20 carbon atoms" means that an alkyl group can contain only 1 carbon atom, 2 carbon atoms, 3 carbon atoms, etc., up to and including 20 carbon atoms (although the term "alkyl" also includes instances where no numerical range of carbon atoms is designated).

"Adhesive" or "adhesive compound" as used herein, refers to any substance that can adhere or bond two items together. Implicit in the definition of an "adhesive composition" or "adhesive formulation" is the fact that the composition or formulation is a combination or mixture of more than one species, component or compound, which can include adhesive monomers, oligomers, and/or polymers along with other materials, whereas an "adhesive compound" refers to a single species, such as an adhesive polymer or oligomer.

More specifically, adhesive composition refers to un-cured mixtures in which the individual components in the mixture retain the chemical and physical characteristics of the original individual components of which the mixture is made. Adhesive compositions are typically malleable and may be liquids, paste, gel or another form that can be applied to an item so that it can be bonded to another item.

"Cured adhesive," "cured adhesive composition" or "cured adhesive compound" refers to adhesives components and mixtures obtained from reactive curable original compound(s) or mixture(s) thereof which have undergone a chemical and/or physical changes such that the original compound(s) or mixture(s) is(are) transformed into a solid, substantially non-flowing material. A typical curing process may involve crosslinking.

"Curable" means that an original compound(s) or composition material(s) can be transformed into a solid, substantially non-flowing material by means of chemical reaction, crosslinking, radiation crosslinking, or the like. Thus, adhesive compositions of the invention are curable, but unless otherwise specified, the original compound(s) or composition material(s) is(are) not cured.

"Thermoplastic," as used herein, refers to the ability of a compound, composition or other material (e.g. a plastic) to dissolve in a suitable solvent or to melt to a liquid when heated and freeze to a solid, often brittle and glassy, state when cooled sufficiently.

"Thermoset," as used herein, refers to the ability of a compound, composition or other material to irreversibly "cure" resulting in a single tridimensional network that has greater strength and less solubility compared to the non-cured product. Thermoset materials are typically polymers that may be cured, for example, through heat (e.g. above 200° Celsius), via a chemical reaction (e.g. epoxy ring opening, free-radical polymerization, etc.), or through irradiation (e.g. visible light, U.V., or X-ray irradiation).

Thermoset materials, such as thermoset polymers or resins, are typically liquid or malleable forms prior to curing, and therefore may be molded or shaped into their final form, and/or used as adhesives. Curing transforms the thermoset resin into a rigid infusible and insoluble solid or rubber by a cross-linking process. Thus, energy and/or catalysts are typically added that cause the molecular chains to react at chemically active sites (unsaturated or epoxy sites, for example), linking the polymer chains into a rigid, 3-D structure. The cross-linking process forms molecules with a higher molecular weight and resultant higher melting point. During the reaction, when the molecular weight of the polymer has increased to a point such that the melting point is higher than the surrounding ambient temperature, the polymer becomes a solid material.

"Cross-linking," as used herein, refers to the attachment of two or more oligomer or longer polymer chains by bridges of an element, a molecular group, a compound, or another oligomer or polymer. Crosslinking may take place upon heating; some crosslinking processes may also occur at room temperature or a lower temperature. As cross-linking density is increased, the properties of a material can be changed from thermoplastic to thermosetting.

As used herein, "B-stageable" refers to the properties of an adhesive having a first solid phase followed by a tacky rubbery stage at elevated temperature, followed by yet another solid phase at an even higher temperature. The transition from the tacky rubbery stage to the second solid phase is thermosetting. However, prior to thermosetting, the material behaves similarly to a thermoplastic material. Thus, such adhesives allows for low lamination temperatures while providing high thermal stability.

A "die" or "semiconductor die" as used herein, refers to a small block of semiconducting material, on which a functional circuit is fabricated.

A "flip-chip" semiconductor device is one in which a semiconductor die is directly mounted to a wiring substrate, such as a ceramic or an organic printed circuit board. Conductive terminals on the semiconductor die, usually in the form of solder bumps, are directly physically and electrically connected to the wiring pattern on the substrate without use of wire bonds, tape-automated bonding (TAB), or the like. Because the conductive solder bumps making connections to the substrate are on the active surface of the die or chip, the die is mounted in a face-down manner, thus the name "flip-chip."

"Underfill," "underfill composition" and "underfill material" are used interchangeably to refer to a material, typically polymeric compositions, used to fill gaps between a semiconductor component, such as a semiconductor die, and a substrate. "Underfilling" refers to the process of applying an underfill composition to a semiconductor component-substrate interface, thereby filling the gaps between the component and the substrate.

The term "monomer" refers to a molecule that can undergo polymerization or copolymerization thereby contributing constitutional units to the essential structure of a macromolecule (a polymer).

"Polymer" and "polymer compound" are used interchangeably herein, to refer generally to the combined the products of a single chemical polymerization reaction. Polymers are produced by combining monomer subunits into a covalently bonded chain. Polymers that contain only a single type of monomer are known as "homopolymers," while polymers containing a mixture of monomers are known as "copolymers."

The term "copolymers" is inclusive of products that are obtained by copolymerization of two monomer species, those obtained from three monomers species (terpolymers), those obtained from four monomers species (quaterpolymers), etc. It is well known in the art that copolymers synthesized by chemical methods include, but are not limited to, molecules with the following types of monomer arrangements:

alternating copolymers, which contain regularly alternating monomer residues;

periodic copolymers, which have monomer residue types arranged in a repeating sequence;

random copolymers, which have a random sequence of monomer residue types;

statistical copolymers, which have monomer residues arranged according to a known statistical rule;

block copolymers, which have two or more homopolymer subunits linked by covalent bonds. The blocks of homopolymer within block copolymers, for example, can be of any length and can be blocks of uniform or variable length. Block copolymers with two or three distinct blocks are called diblock copolymers and triblock copolymers, respectively; and star copolymers, which have chains of monomer residues having different constitutional or configurational features that are linked through a central moiety.

The skilled artisan will appreciate that a single copolymer molecule may have different regions along its length that can be characterized as an alternating, periodic, random, etc. A copolymer product of a chemical polymerization reaction may contain individual polymeric fragments that each differ in the arrangement of monomer units. The skilled artisan will further be knowledgeable in methods for synthesizing each of these types of copolymers, and for varying reaction conditions to favor one type over another.

Furthermore, the length of a polymer chain according to the present invention, will typically vary over a range or average size produced by a particular reaction. The skilled artisan will be aware, for example, of methods for controlling the average length of a polymer chain produced in a given reaction and also of methods for size-selecting polymers after they have been synthesized.

Unless a more restrictive term is used, polymer is intended to encompass homopolymers, and copolymers having any arrangement of monomer subunits as well as copolymers containing individual molecules having more than one arrangement. With respect to length, unless otherwise indicated, any length limitations recited for the polymers described herein are to be considered averages of the lengths of the individual molecules in polymer.

"Thermoplastic elastomer" or "TPE", as used herein refers to a class of copolymers which consist of materials with both thermoplastic and elastomeric properties.

"Hard blocks" or "hard segments" as used herein refer to a block of a copolymer (typically a thermoplastic elastomer) that is hard at room temperature by virtue of a of high melting point ($T_m$) or $T_g$. By contrast, "soft blocks" or "soft segments" have a $T_g$ below room temperature.

As used herein, "oligomer" or "oligomeric" refers to a polymer having a finite and moderate number of repeating monomers structural units. Oligomers of the invention typically have 2 to about 100 repeating monomer units; frequently 2 to about 30 repeating monomer units; and often 2 to about 10 repeating monomer units; and usually have a molecular weight up to about 3,000.

The skilled artisan will appreciate that oligomers and polymers may, depending on the availability of polymerizable groups or side chains, subsequently be incorporated as monomers in further polymerization or crosslinking reactions.

As used herein, "aliphatic" refers to any alkyl, alkenyl, cycloalkyl, or cycloalkenyl moiety.

"Aromatic hydrocarbon" or "aromatic" as used herein, refers to compounds having one or more benzene rings.

"Alkane," as used herein, refers to saturated straight-chain, branched or cyclic hydrocarbons having only single bonds.

Alkanes have general formula $C_nH_{2n+2}$. "Cycloalkane," refers to an alkane having one or more rings in its structure.

As used herein, "alkyl" refers to straight or branched chain hydrocarbyl groups having from 1 up to about 500 carbon atoms. The terms "alkyl" and "substituted alkyl" include, respectively, substituted and unsubstituted $C_1$-$C_{500}$ straight chain saturated aliphatic hydrocarbon groups, substituted and unsubstituted $C_2$-$C_{200}$ straight chain unsaturated aliphatic hydrocarbon groups, substituted and unsubstituted $C_4$-$C_{100}$ branched saturated aliphatic hydrocarbon groups, substituted and unsubstituted $C_1$-$C_{500}$ branched unsaturated aliphatic hydrocarbon groups.

For example, the definition of "alkyl" includes but is not limited to: methyl (Me), ethyl (Et), propyl (Pr), butyl (Bu), pentyl, hexyl, heptyl, octyl, nonyl, decyl, undecyl, ethenyl, propenyl, butenyl, penentyl, hexenyl, heptenyl, octenyl, nonenyl, decenyl, undecenyl, isopropyl (i-Pr), isobutyl (i-Bu), tert-butyl (t-Bu), sec-butyl (s-Bu), isopentyl, neopentyl, cyclopropyl, cyclobutyl, cyclopentyl, cyclohexyl, cycloheptyl, cyclooctyl, cyclopentenyl, cyclohexenyl, cycloheptenyl, cyclooctenyl, methylcyclopropyl, ethylcyclohexenyl, butenylcyclopentyl, adamantyl, norbornyl and the like.

"Substituted alkyl" refers to alkyl moieties bearing substituents that include but are not limited to alkyl, alkenyl, alkynyl, hydroxy, oxo, alkoxy, mercapto, cycloalkyl, substituted cycloalkyl, heterocyclic, substituted heterocyclic, aryl, substituted aryl (e.g., aryl$C_{1-10}$alkyl or aryl$C_{1-10}$alkyloxy), heteroaryl, substituted heteroaryl (e.g., heteroaryl$C_{1-10}$alkyl), aryloxy, substituted aryloxy, halogen, haloalkyl (e.g., trihalomethyl), cyano, nitro, nitrone, amino, amido, carbamoyl, =O, =CH—, —C(O)H, —C(O)O—, —C(O)—, —S—, —S(O)$_2$, —C(O)—O—, —NR—C(O), —NR—C(O)—NR, —OC(O)—NR, where R is H or lower alkyl, acyl, oxyacyl, carboxyl, carbamate, sulfonyl, sulfonamide, sulfuryl, $C_{1-10}$alkylthio, aryl$C_{1-10}$alkylthio, $C_{1-10}$alkylamino, aryl$C_{1-10}$alkylamino, N-aryl-N-$C_{1-10}$-alkylamino, $C_{1-10}$alkyl carbonyl, aryl$C_{1-10}$alkylcarbonyl, $C_{1-10}$alkylcarboxy, aryl $C_{1-10}$alkylcarboxy, $C_{1-10}$alkyl carbonylamino, aryl $C_{1-10}$alkylcarbonylamino, tetrahydrofuryl, morpholinyl, piperazinyl, and hydroxypyronyl.

As used herein, "cycloalkyl" refers to cyclic ring-containing groups containing in the range of about 3 up to about 20 carbon atoms, typically 3 to about 15 carbon atoms. In certain embodiments, cycloalkyl groups have in the range of about 4 up to about 12 carbon atoms, and in yet further embodiments, cycloalkyl groups have in the range of about 5 up to about 8 carbon atoms. and "substituted cycloalkyl" refers to cycloalkyl groups further bearing one or more substituents as set forth below.

As used herein, the term "aryl" represents an unsubstituted, mono-, di- or trisubstituted monocyclic, polycyclic, biaryl aromatic groups covalently attached at any ring position capable of forming a stable covalent bond, certain preferred points of attachment being apparent to those skilled in the art (e.g., 3-phenyl, 4-naphtyl and the like). The aryl substituents are independently selected from the group consisting of halo, —OH, —SH, —CN, —NO$_2$, trihalomethyl, hydroxypyronyl, $C_{1-10}$alkyl, aryl$C_{1-10}$alkyl, $C_{1-10}$alkyloxy$C_{1-10}$alkyl, aryl $C_{1-10}$alkyloxy$C_{1-10}$alkyl, $C_{1-10}$alkylthio$C_{1-10}$alkyl, aryl $C_{1-10}$alkylthio$C_{1-10}$alkyl, $C_{1-10}$alkylamino$C_{1-10}$alkyl, aryl$C_{1-10}$alkylamino$C_{1-10}$alkyl, N-aryl-N—$C_{1-10}$alkylamino$C_{1-10}$alkyl, $C_{1-10}$alkylcarbonyl$C_{1-10}$alkyl, aryl $C_{1-10}$alkylcarbonyl $C_{1-10}$alkylcarboxy$C_{1-10}$alkyl, aryl$C_{1-10}$alkylcarboxy$C_{1-10}$alkyl, $C_{1-10}$alkylcarbonylamino$C_{1-10}$alkyl, and aryl$C_{1-10}$alkylcarbonylamino$C_{1-10}$alkyl.

Some specific examples of moieties encompassed by the definition of "aryl" include but are not limited to phenyl, biphenyl, naphthyl, dihydronaphthyl, tetrahydronaphthyl, indenyl, indanyl, azulenyl, anthryl, phenanthryl, fluorenyl, pyrenyl and the like. "Substituted aryl" refers to aryl groups further bearing one or more substituents as set forth below.

As used herein, "arylene" refers to a divalent aryl moiety. "Substituted arylene" refers to arylene moieties bearing one or more substituents as set forth above.

As used herein, "alkylaryl" refers to alkyl-substituted aryl groups and "substituted alkylaryl" refers to alkylaryl groups further bearing one or more substituents as set forth below.

As used herein, "arylalkyl" refers to aryl-substituted alkyl groups and "substituted arylalkyl" refers to arylalkyl groups further bearing one or more substituents as set forth below. Some examples of included but are not limited to (4-hydroxyphenyl)ethyl, or (2-aminonaphthyl)hexenyl.

As used herein, "arylalkenyl" refers to aryl-substituted alkenyl groups and "substituted arylalkenyl" refers to arylalkenyl groups further bearing one or more substituents as set forth below.

As used herein, "arylalkynyl" refers to aryl-substituted alkynyl groups and "substituted arylalkynyl" refers to arylalkynyl groups further bearing one or more substituents as set forth below.

As used herein, "aroyl" refers to aryl-carbonyl species such as benzoyl and "substituted aroyl" refers to aroyl groups further bearing one or more substituents as set forth below.

As used herein, "hetero" refers to groups or moieties containing one or more heteroatoms such as N, O, Si and S. Thus, for example "heterocyclic" refers to cyclic (i.e., ring-containing) groups having e.g. N, O, Si or S as part of the ring structure, and having in the range of 3 up to 14 carbon atoms. "Heteroaryl" and "heteroalkyl" moieties are aryl and alkyl groups, respectively, containing e.g. N, O, Si or S as part of their structure. The terms "heteroaryl", "heterocycle" or "heterocyclic" refer to a monovalent unsaturated group having a single ring or multiple condensed rings, from 1 to 8 carbon atoms and from 1 to 4 hetero atoms selected from nitrogen, sulfur or oxygen within the ring.

The definition of heteroaryl includes but is not limited to thienyl, benzothienyl, isobenzothienyl, 2,3-dihydrobenzothienyl, furyl, pyranyl, benzofuranyl, isobenzofuranyl, 2,3-dihydrobenzofuranyl, pyrrolyl, pyrrolyl-2,5-dione, 3-pyrrolinyl, indolyl, isoindolyl, 3H-indolyl, indolinyl, indolizinyl, indazolyl, phthalimidyl (or isoindoly-1,3-dione), imidazolyl. 2H-imidazolinyl, benzimidazolyl, pyridyl, pyrazinyl, pyradazinyl, pyrimidinyl, triazinyl, quinolyl, isoquinolyl, 4H-quinolizinyl, cinnolinyl, phthalazinyl, quinazolinyl, quinoxalinyl, 1,8-naphthyridinyl, pteridinyl, carbazolyl, acridinyl, phenazinyl, phenothiazinyl, phenoxazinyl, chromanyl, benzodioxolyl, piperonyl, purinyl, pyrazolyl, triazolyl, tetrazolyl, thiazolyl, isothiazolyl, benzthiazolyl, oxazolyl, isoxazolyl, benzoxazolyl, oxadiazolyl, thiadiazolyl, pyrrolidinyl-2,5-dione, imidazolidinyl-2,4-dione, 2-thioxo-imidazolidinyl-4-one, imidazolidinyl-2,4-dithione, thiazolidinyl-2,4-dione, 4-thioxo-thiazolidinyl-2-one, piperazinyl-2,5-dione, tetrahydro-pyridazinyl-3,6-dione, 1,2-dihydro-[1,2,4]tetrazinyl-3,6-dione, [1,2,4,5] tetrazinanyl-3,6-dione, dihydro-pyrimidinyl-2,4-dione, pyrimidinyl-2,4,6-trione, 1H-pyrimidinyl-2,4-dione, 5-iodo-1H-pyrimidinyl-2,4-dione, 5-chloro-1H-pyrimidinyl-2,4-dione, 5-methyl-1H-pyrimidinyl-2,4-dione, 5-isopropyl-1H-pyrimidinyl-2,4-dione, 5-propynyl-1H-pyrimidinyl-2,4-dione, 5-trifluoromethyl-1H-pyrimidinyl-2,4-dione, 6-amino-9H-purinyl, 2-amino-9H-purinyl, 4-amino-1H-pyrimidinyl-2-one, 4-amino-5-fluoro-1H-pyrimidinyl-2-one, 4-amino-5-methyl-1H-pyrimidinyl-2-one, 2-amino-1,9-dihydro-purinyl-6-one, 1,9-dihydro-purinyl-6-one, 1H-[1,2,4] triazolyl-3-carboxylic acid amide, 2,6-diamino-N.sub.6-cyclopropyl-9H-purinyl, 2-amino-6-(4-methoxyphenylsulfanyl)-9H-purinyl, 5,6-dichloro-1H-benzoimidazolyl, 2-isopropylamino-5,6-dichloro-1H-benzoimidazolyl, 2-bromo-5,6-dichloro-1H-benzoimidazolyl, and the like. Furthermore, the term "saturated heterocyclic" represents an unsubstituted, mono-, di- or trisubstituted monocyclic, polycyclic saturated heterocyclic group covalently attached at any ring position capable of forming a stable covalent bond, certain preferred points of attachment being apparent to those skilled in the art (e.g., 1-piperidinyl, 4-piperazinyl and the like).

Hetero-containing groups may also be substituted. For example, "substituted heterocyclic" refers to a ring-containing group having in the range of 3 up to 14 carbon atoms that contains one or more heteroatoms and also bears one or more substituents, as set forth above. Examples of substituents include, but are not limited to halo, —OH, —SH, —CN, —NO$_2$, trihalomethyl, hydroxypyronyl, $C_{1-10}$alkyl, aryl $C_{1-10}$alkyl, $C_{1-10}$alkyloxy$C_{1-10}$alkyl, aryl$C_{1-10}$alkyloxy $C_{1-10}$alkyl, $C_{1-10}$alkylthio$C_{1-10}$alkyl, aryl$C_{1-10}$alkylthio $C_{1-10}$alkyl, $C_{1-10}$alkylamino$C_{1-10}$alkyl, aryl$C_{1-10}$alkylamino $C_{1-10}$alkyl, N-aryl-N—$C_{1-10}$alkylamino$C_{1-10}$alkyl, $C_{1-10}$alkylcarbonyl$C_{1-10}$alkyl, aryl$C_{1-10}$alkylcarbonyl $C_{1-10}$alkyl, $C_{1-10}$alkylcarboxy$C_{1-10}$alkyl, aryl$C_{1-10}$alkylcarboxy$C_{1-10}$alkyl $C_{1-10}$alkylcarbonylamino$C_{1-10}$alkyl, and aryl$C_{1-10}$alkylcarbonylamino $C_{1-10}$alkyl.

As used herein, the term "phenol" includes compounds having one or more phenolic functions per molecule. The terms aliphatic, cycloaliphatic and aromatic, when used to describe phenols, refers to phenols to which aliphatic, cycloaliphatic and aromatic residues or combinations of these backbones are attached by direct bonding or ring fusion.

As used herein, "alkenyl," "alkene" or "olefin" refers to straight or branched chain unsaturated hydrocarbyl groups having at least one carbon-carbon double bond, and having in the range of about 2 up to 500 carbon atoms. In certain embodiments, alkenyl groups have in the range of about 5 up to about 250 carbon atoms, 5 up to about 100 carbon atoms, 5 up to about 50 carbon atoms or 5 up to about 25 carbon atoms. In other embodiments, alkenyl groups have in the range of about 6 up to about 500 carbon atoms, 8 up to about 500 carbon atoms, 10 up to about 500 carbon atoms or 20 up to about 500 carbon atoms or 50 up to about 500 carbon atoms. In yet further embodiments, alkenyl groups have in the range of about 6 up to about 100 carbon atoms, 10 up to about 100 carbon atoms, 20 up to about 100 carbon atoms or 50 up to about 100 carbon atoms, while in other embodiments, alkenyl groups have in the range of about 6 up to about 50 carbon atoms, 6 up to about 25 carbon atoms, 10 up to about 50 carbon atoms, or 10 up to about 25 carbon atoms. "Substituted alkenyl" refers to alkenyl groups further bearing one or more substituents as set forth above.

As used herein, "alkylene" refers to a divalent alkyl moiety, and "oxyalkylene" refers to an alkylene moiety containing at least one oxygen atom instead of a methylene ($CH_2$) unit. "Substituted alkylene" and "substituted oxyalkylene" refer to alkylene and oxyalkylene groups further bearing one or more substituents as set forth above.

As used herein, "alkynyl" refers to straight or branched chain hydrocarbyl groups having at least one carbon-carbon triple bond, and having in the range of 2 up to about 100 carbon atoms, and "substituted alkynyl" refers to alkynyl groups further bearing one or more substituents as set forth below.

As used herein, "oxiranylene" refers to divalent moieties having the structure:

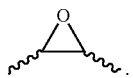

As used herein, "arylene" refers to a divalent aryl moiety. "Substituted arylene" refers to arylene moieties bearing one or more substituents as set forth above.

As used herein, "acyl" refers to alkyl-carbonyl species.

"Allyl" as used herein, refers to refers to a compound bearing at least one moiety having the structure:

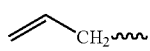

"Imide" as used herein, refers to a functional group having two carbonyl groups bound to a primary amine or ammonia. The general formula of an imide of the invention is:

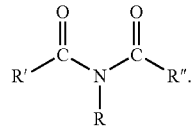

"Polyimides" are polymers of imide-containing monomers. Polyimides are typically linear or cyclic. Non-limiting examples of linear and cyclic (e.g. an aromatic heterocyclic polyimide) polyimides are shown below for illustrative purposes.

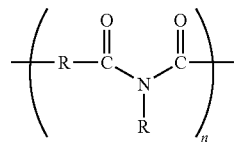

Linear Polyimide

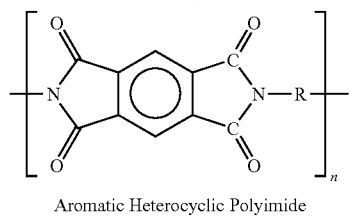

Aromatic Heterocyclic Polyimide

"Maleimide," as used herein, refers to an N-substituted maleimide having the formula as shown below:

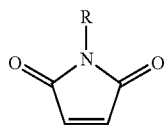

where R is an aromatic, herteroaromatic, aliphatic, or polymeric moiety.

"Bismaleimide" or "BMI", as used herein, refers to a polyimide having the general structure shown below:

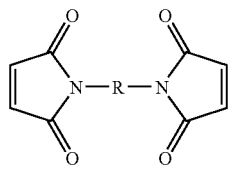

where R is an aromatic, herteroaromatic, aliphatic, or polymeric moiety.

BMIs can cure through an addition rather than a condensation reaction, thus avoiding problems resulting from the formation of volatiles. BMIs can be produced by a vinyl-type polymerization of a pre-polymer terminated with two maleimide groups.

As used herein, the term "maleate" refers to a compound bearing at least one moiety having the structure:

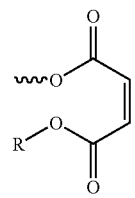

wherein R=lower alkyl.

As used herein, the term "acyloxy benzoate" or "phenyl ester" refers to a compound bearing at least one moiety having the structure:

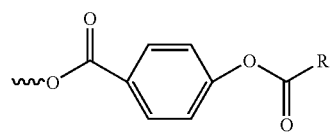

wherein R=H, lower alkyl, or aryl.

As used herein, the term "acrylate" refers to a compound bearing at least one moiety having the structure:

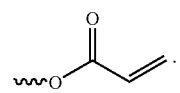

As used herein, the term "acrylamide" refers to a compound bearing at least one moiety having the structure:

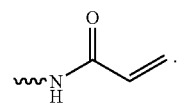

As used herein, the term "methacrylate" refers to a compound bearing at least one moiety having the structure:

As used herein, the term "methacrylamide" refers to a compound bearing at least one moiety having the structure:

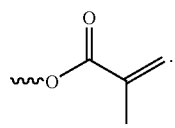

As used herein, the term "citraconimide" refers to a compound bearing at least one moiety having the structure:

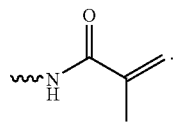

"Itaconate", as used herein refers to a compound bearing at least one moiety having the structure:

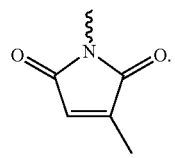

As used herein, the terms "halogen," "halide," or "halo" include fluorine, chlorine, bromine, and iodine.

As used herein, "siloxane" refers to any compound containing a Si—O moiety. In certain embodiments, siloxanes of the invention include 2 or more repeating units of Si—O. Exemplary cyclic siloxanes include hexamethylcyclotrisiloxane, octamethylcyclotetrasiloxane, decamethylcyclopentasiloxane, dodecamethylcyclohexasiloxane and the like.

As used herein "epoxy" refers to a thermosetting epoxide polymer that cures by polymerization and crosslinking when mixed with a catalyzing agent or "hardener," also referred to as a "curing agent" or "curative." Epoxies of the present invention include, but are not limited to aliphatic, cycloaliphatic, glycidyl ether, glycidyl ester, glycidyl amine epoxies, and the like, and combinations thereof. Epoxies of the invention include compounds bearing at least one moiety having the structure:

As used herein, the term "oxetane" refers to a compound bearing at least one moiety having the structure:

As used herein, the term "vinyl ether" refers to a compound bearing at least one moiety having the structure:

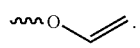

As used herein, the term "vinyl ester" refers to a compound bearing at least one moiety having the structure:

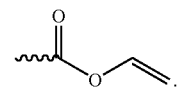

As used herein, "styrenic" refers to a compound bearing at least one moiety having the structure:

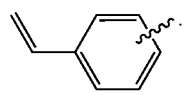

"Oxazoline" as used herein, refers to a compound bearing at least one moiety having the structure:

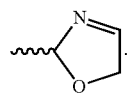

"Benzoxazine" as used herein, refers to a compound bearing at least one moiety having the structure:

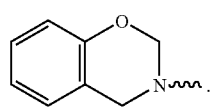

"Fumarate" as used herein, refers to a compound bearing at least one moiety having the structure:

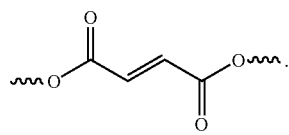

"Propargyl" as used herein, refers to a compound bearing at least one moiety having the structure:

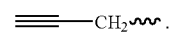

"Cyanate" as used herein, refers to a compound bearing at least one moiety having the structure:

As used herein, "norbornyl" refers to a compound bearing at least one moiety having the structure:

As used herein, the term "free radical initiator" refers to any chemical species which, upon exposure to sufficient energy (e.g., light, heat, or the like), decomposes into parts which are uncharged, but every one of such part possesses at least one unpaired electron.

As used herein, the term "coupling agent" refers to chemical species that are capable of bonding to a mineral surface and which also contain polymerizably reactive functional group(s) so as to enable interaction with the adhesive composition. Coupling agents thus facilitate linkage of the die-attach paste to the substrate to which it is applied.

"Diamine," as used herein, refers generally to a compound or mixture of compounds, where each species has 2 amine groups.

A "diol" according to the present invention, is a compound containing two hydroxyl groups (—OH groups); while "polyol" refers to alcohols containing multiple hydroxyl groups.

The term "solvent," as used herein, refers to a liquid that dissolves a solid, liquid, or gaseous solute, resulting in a solution. "Co-solvent" refers to a second, third, etc. solvent used with a primary solvent.

As used herein, "alcohol catalyst" refers to an alcohol or combination of alcohols that, when added to a chemical reaction, has the effect of accelerating, increasing the rate or yield of the reaction without being consumed by the overall reaction. Typically, an alcohol catalyst will contain a single alcohol, but mixtures comprising two or more alcohols are contemplated for use in the present invention.

As used herein, "acid catalyst" refers to any acidic substance or compound that, when added to a chemical reaction, has the effect of accelerating, increasing the rate or yield of the reaction without being consumed by the overall reaction. Typically, an acid catalyst will contain a single acid, but mixtures comprising two or more acids are contemplated for use in the present invention. Acid catalysts of the invention can be soluble or insoluble. For example, polymer-bound acid catalysts may conveniently be used in the methods of the invention and then easily removed e.g. by gravity filtration.

"Friedel-Crafts alkylation" is an electrophilic aromatic substitution that involves the alkylation of an aromatic ring with an alkyl halide using a strong Lewis acid catalyst. A typical reaction scheme for alkylation of a benzene ring is shown below:

Friedel Crafts Alkylation Scheme

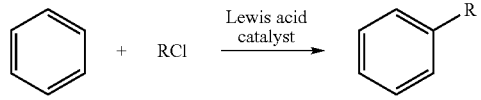

"Prilezhaev reaction" is a method for synthesizing epoxy compounds are by reacting olefins with peroxides; the later provide an oxygen atom that becomes a part of the resulting epoxy compound. Some peroxide reagents that may be used include hydrogen peroxide, peroxycarboxylic acids, and alkyl hydroperoxides. The Prilezhaev reaction may be schematically illustrated by the following reaction scheme demonstrating the formation of an epoxy compound from styrene:

Prilezhaev Reaction Scheme

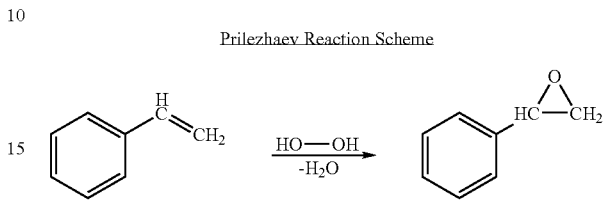

"Glass transition temperature" or "$T_g$": is used herein to refer to the temperature at which an amorphous solid, such as a polymer, becomes brittle on cooling, or soft on heating. More specifically, it defines a pseudo second order phase transition in which a supercooled melt yields, on cooling, a glassy structure and properties similar to those of crystalline materials e.g. of an isotropic solid material.

"Modulus" or "Young's modulus" as used herein, is a measure of the stiffness of a material. Within the limits of elasticity, modulus is the ratio of the linear stress to the linear strain which can be determined from the slope of a stress-strain curve created during tensile testing.

The "Coefficient of Thermal Expansion" or "CTE" is a term of art describing a thermodynamic property of a substance. The CTE relates a change in temperature to the change in a material's linear dimensions. As used herein "$\alpha_1$ CTE" or "$\alpha_1$," refers to the CTE before the $T_g$, while "$\alpha_2$ CTE" refers to the CTE after the $T_g$.

"Thixotropy" as used herein, refers to the property of a material which enables it to stiffen or thicken in a relatively short time upon standing, but upon agitation or manipulation to change to low-viscosity fluid; the longer the fluid undergoes shear stress, the lower its viscosity. Thixotropic materials are therefore gel-like at rest but fluid when agitated and have high static shear strength and low dynamic shear strength, at the same time.

"Thermogravimetric analysis" or "TGA" refers to a method of testing and analyzing a material to determine changes in weight of a sample that is being heated in relation to change in temperature. "Decomposition onset" refers to a temperature when the loss of weight in response to the increase of the temperature indicates that the sample is beginning to degrade.

The present invention is based on the discovery that the compounds and compositions described herein are useful as adhesives for the electronic packaging industry. The invention provides functionalized styrene oligomers and polymers and methods for use thereof. Invention oligomers and polymers are readily prepared using Friedel-Crafts post-reactions on styrenic-based macromolecules.

The invention provides styrene oligomers or polymers functionalized via Friedel-Crafts alkylation. In general, a functionalized moiety can be added to a pendant aromatic ring of styrene oligomers or polymers. The functional moiety is typically one that cannot itself react or participate in the alkylation reaction. In some cases, however, it is possible to graft a functional group on to styrene that is itself also capable of participating in Friedel-Crafts alkylation. In such cases, the reaction conditions are selected to give only the desired product. By way of example, an allyl functional moiety can be grafted onto a polystyrene backbone using either allyl chloride or allyl alcohol. All three reactive centers produced in the reaction (i.e. chloride, hydroxyl, and alkene) are capable of generating carbonium ions in the presence of an Lewis acid catalyst, thereby leading to alkylation of the pendant benzene rings. Conditions that are known to those having ordinary skill in the art may be selected, however, wherein the alkene itself remains intact. Electron poor double bonds will not participate in the Friedel-Crafts alkylation, so suitably substituted acrylates, methacrylates, maleimides, and the like, may be grafted to polystyrene backbones.

The polystyrene may itself have bear substitution prior to Friedel-Crafts alkylation. Poly(t-butylstyrene), polymethylstyrene, poly(α-methylstyrene), poly(4-acetoxystyrene), and the like, and co-polymers thereof, may also be used as precursors.

In certain embodiments, a pendant aromatic ring of a styrene oligomer or polymer can be alkylated via Friedel-Crafts chemistry using the unsaturation of an olefinic function to alkylate the aromatic residues. Thus, a wide variety of olefinic functionalities can be added to the styrene oligomers and polymers, to provide useful, reactive oligomers and polymers. In some embodiments, a (meth)allyl group is added to the pendant benzene ring of a styrene oligomer or polymer by using (meth)allyl halide or alcohol, through a pendant halide or hydrohyl residue. Accordingly, a styrene oligomer or polymer having unsaturated moieties (other than possible remaining double bonds of the original monomeric styrene) may be obtained.

In general, a variety of olefin, hydroxy, or halide functional compounds can be added to the pendant aromatic groups of styrene oligomers or polymers. These new derivatives are especially useful where the alkyl group that is introduced has additional (polymerizable) functionality, as shown in the following general Scheme A:

Scheme A:
Functionalization of Styrene-containing Oligomers and Polymers

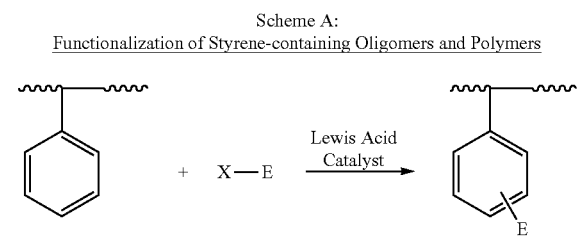

where E is selected from maleimido, acrylate, methacrylate, allyl, methallyl, and oxetane, and X is Cl, Br, I, —OH or α-olefin.

The reaction scheme A of the invention thus provides compounds having a structure represented by formula I:

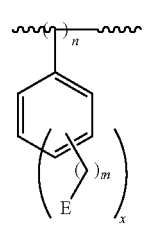

where E is any of maleimido, acrylate, methacrylate, allyl, methallyl, oxetane, a partially or fully epoxidized allyl, a partially or fully epoxidized methallyl; n is an integer having the value between 3 and about 100; m is an integer having the value between 0 and 12; and x is an integer having the value between 1 and 5.

Exemplary functionalized styrene oligomers according to the present include:

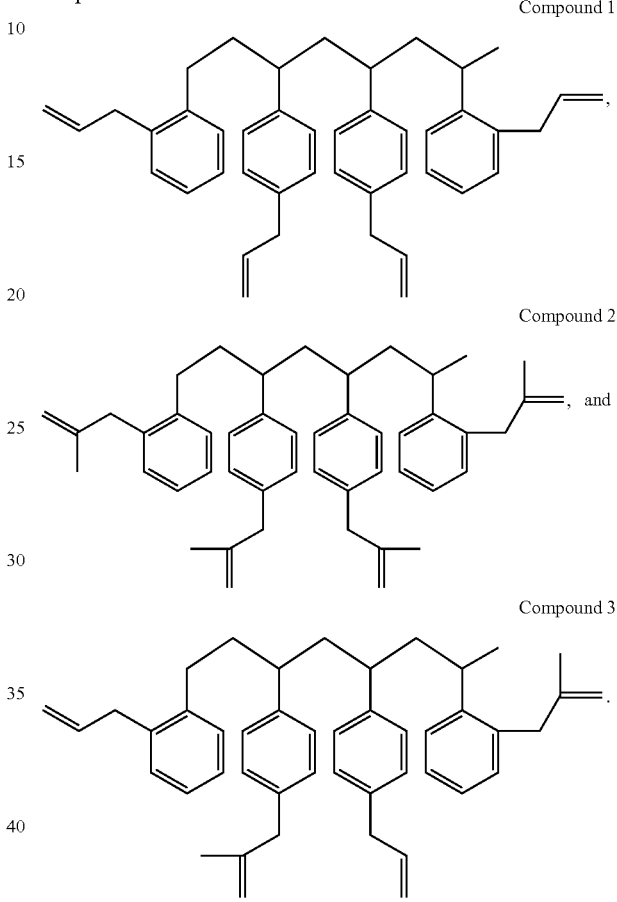

Olefin-substituted styrene oligomers and polymers may further be fully or partially oxidized by methods well known in the art to form epoxy moieties. One typical method of introducing epoxy groups may be by using the Prilezhaev reaction described above. Those having ordinary skill in the art can selected the conditions under which the epoxidation may be carried out.

Exemplary epoxies of the functionalized styrene oligomers according to the present invention include Compounds 4-6, below:

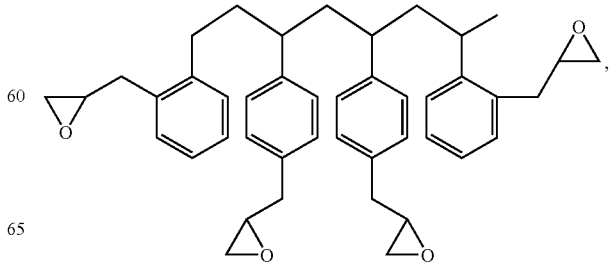

Compound 5

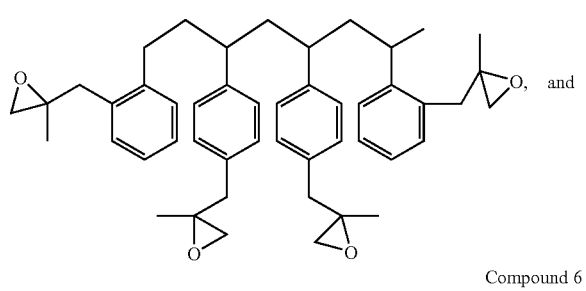

and

Compound 6

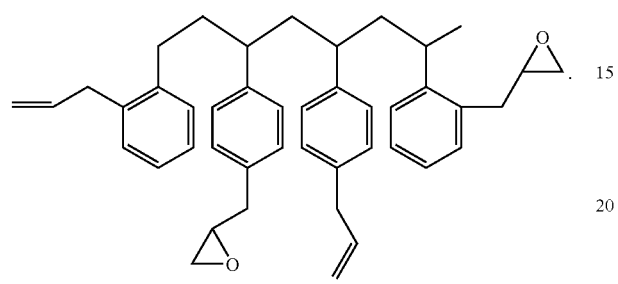

Epoxy compounds of the invention, such as Compounds 4-6, have certain features advantageous for adhesives in the electronics and other industries. The presence of the aromatic ring of the styrene moieties in a beta position relative to the epoxy oxirane ring makes these epoxies more reactive toward polymerization than conventional aliphatic epoxies. The absence of a beta oxygen makes these epoxy compounds less hydrophilic than a glycidyl ether epoxy of a similar equivalent weight. The partially epoxidized functional oligomers are essentially hybrid monomers that can participate in the rich chemistry of epoxy compounds as well as in free radical cures, ene and Diels-Alder reactions in which allyl and methallyl functional groups can participate.

Alkylation of Oligomer and Polymer Chains

The polystyrene segments that are alkylated by the methods of the invention (Scheme A) may be pendant from block, triblock, star or random oligomer or polymer chains. An example of a polymer chain suitable for alkylation according to the present invention is the well-known thermoplastic elastomer polymers (TPEs) based on polystyrene hard segments and polyolefin (preferably hydrogenated) soft segments.

Polystyrene based TPEs include triblock, multiblock, and star polymers in which the hard segments consist of polystyrene and the soft segments consist of polybutadiene (PBD) or hydrogenated polybutadiene. The non-hydrogenated PBD type TPEs are not suitable for Friedel-Crafts functionalization according to the present invention because the unsaturation in the PBD segments would also graft to the polystyrene blocks and thus yield gelled, unusable products. Hydrogenated versions of these TPEs, however, are suitable for the functionalization of the present invention by methods of the invention set forth in Scheme A. The polymer products of such functionalization represented by formulae II and III:

where A is polymer block represented by structural formula I (where E is any of maleimido, acrylate, methacrylate, allyl, methallyl, epoxy, or oxetane), B is a hydrogenated polybutadiene, and y is 1 to 100.

As described above for Compounds of formula I, suitable olefin-substituted styrene oligomers and polymers according to formulae II and III can further be fully or partially oxidized by methods well known in the art to give epoxy functional compounds represented by formulae IV and V:

where A' is a fully or partially expoxidized form of a polymer block represented by structural formula I (i.e., where E is any of a partially or fully epoxidized maleimido, a partially or fully epoxidized acrylate, a partially or fully epoxidized methacrylate, a partially or fully epoxidized allyl, a partially or fully epoxidized methallyl, or a partially or fully epoxidized oxetane); B is a hydrogenated polybutadiene, and y is 1 to 100.

In one embodiment, the polymer products of functionalization and epoxidation thereof, can be represented by formulae VI and VII:

VI

Hydrogenated Polybutadiene Core

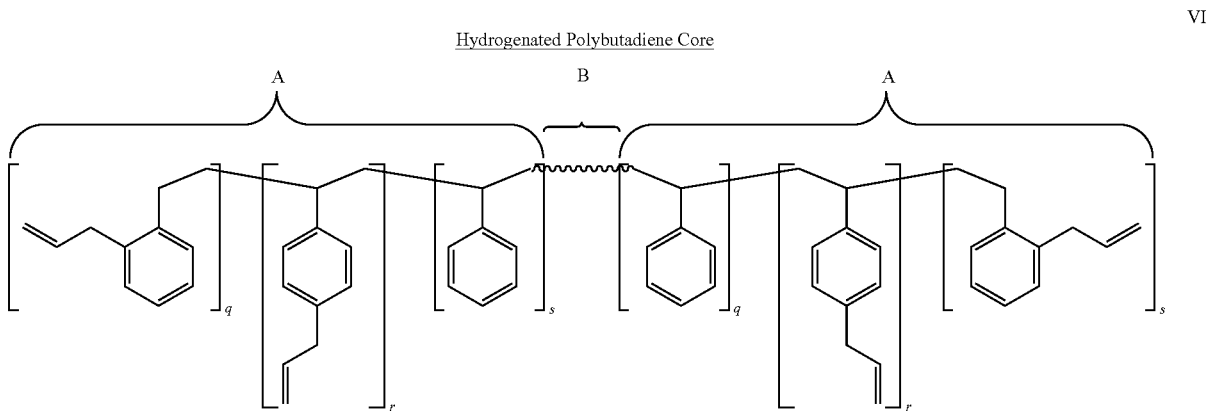

VII

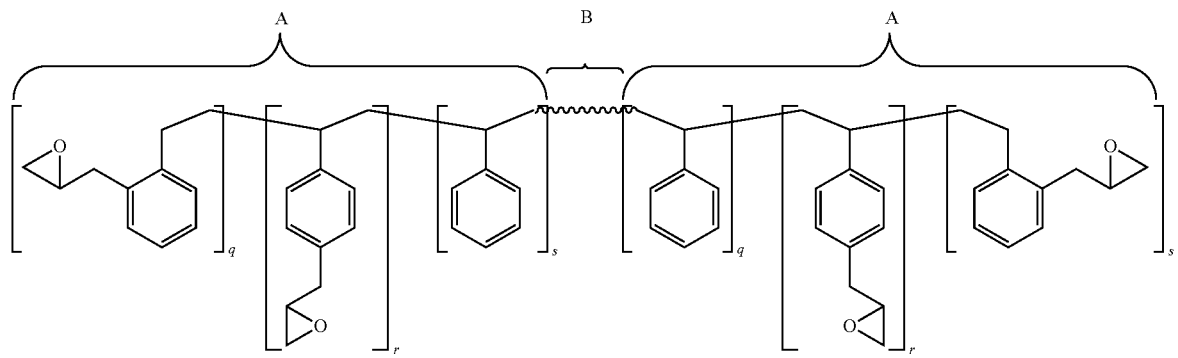
Hydrogenated Polybutadiene Core where each q, r and s is independently 0 to about 60; and the sum of q+r+s is about 15 to about 60, with the proviso that the sum of q+r is at least 1.

A representative functionalized triblock TPE according to the invention is shown below:

Compound 7

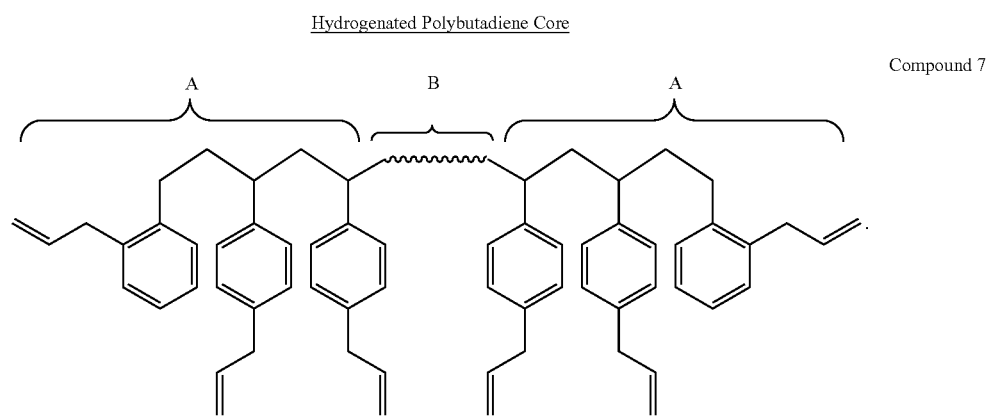
Hydrogenated Polybutadiene Core

This representative allyl functional TPE (Compound 7) can furthermore be oxidized to the corresponding polyepoxy (Compound 8) shown below:

Compound 8

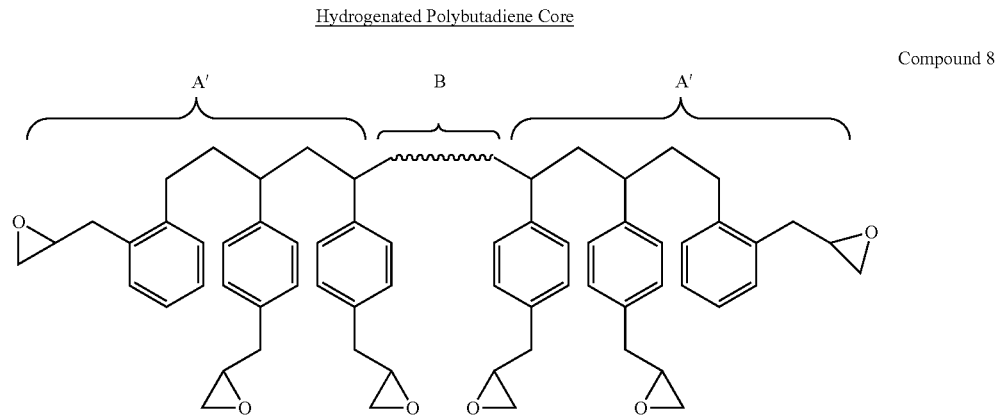
Hydrogenated Polybutadiene Core

The compounds described herein may be used alone in adhesive compositions or added to available resins as a toughening or cross-linking agent. The compound of the invention will be present in curable adhesive compositions in an amount from 0.05 to 98 weight percent (wt %) based on the organic components present (excluding any fillers). In one embodiment, the compound of the invention may be used as the sole thermoset monomer of an adhesive composition. In another embodiment, the compound of the invention may be combined with other thermoset monomers to make a fully formulated adhesive or matrix resin. Thus, in another embodiment of the invention, there is provided an adhesive composition including a compound of the invention and at least one curing initiator.

Additional embodiments of the invention include adhesive bonded structures containing curable ester-linked compound adhesive compositions. Non-limiting examples of the adhesive bonded structures include electronic components bonded to a substrate, and circuit components bonded to printed wire boards.

The compounds of this invention are also useful in a variety of other applications. Invention compounds can be used in automotive, marine, and aerospace coatings, matrix resins and adhesives. The properties of certain invention compounds make them especially suitable for use in advanced composite matrix resins and adhesives. Invention compounds can therefore be used as performance additives that are formulated into composite matrix resins for sports equipment, automotive bodies, and boat construction. The compounds of this invention have particularly attractive properties for use in airplane structural component manufacture where high strength, temperature resistance, moisture resistance, and toughness are critical performance criteria. Furthermore, the compounds of this invention are suitable for use in adhesives or matrix resins in diverse industrial, biomedical, and civil construction applications such as bridge building materials, windmill matrix resins, thread-lock adhesives, dental bonding and filling products, and building materials.

Compositions Containing Functionalized Styrene Compounds

The present invention provides compositions containing at least one functionalized styrene compound according to formula I, above. The compounds of the invention may be used independently as an adhesive or may be combined with other materials and reagents to prepare adhesive compositions. In certain embodiments, the functionalized styrene compounds and/or epoxidized forms thereof, may be combined with other adhesives and/or resins to prepare adhesive compositions. A compound of the invention may be used as the sole monomer of an adhesive composition of the invention. In other embodiments, the compounds of the invention may be combined with other monomers to make a fully formulated adhesive composition.

In certain embodiments of the invention, a compound according to formula I is present in a composition, such as an adhesive composition, in an amount from 0.5 weight percent (wt %) to about 98 wt %, based on the total weight of the composition. Typically, the composition will contain an amount of at least one compound according to formula I equal to at least about 5 wt %, often at least about 10 wt %, frequently at least about 20 wt %, and in some embodiments at least about 40 wt % based on the total weight of the composition.

In another embodiment of the invention, the composition containing the compound of formula I includes at least one co-monomer, which is typically present in an amount from 10 wt % to about 90 wt %, based on the total weight of the composition. In some aspects of the invention, the composition will contain an amount of the co-monomer equal to at least about 15 wt %%, often at least about 20 wt %, frequently at least about 25 wt %, and in some embodiments at least about 30 wt % based on the total weight of the composition. Co-monomers suitable for use in the compositions of the invention include, but are not limited to, acrylates, acrylamides, methacrylates, methacrylamides, cyanate esters, maleimides, vinyl ethers, vinyl esters, styrenic compounds, allyl functional compounds, epoxies, epoxy curatives, and olefins.

Curing Initiators. In certain embodiments, the present invention provides compositions, such as adhesive compositions, including at least one of formula I and at least one curing initiator. The curing initiator is typically present in adhesive compositions of the invention at an amount from 0.1 wt % to about 5 wt %, based on total weight of the composition, and is typically a free-radical initiator. In some embodiments, the curing initiator is present at least about 0.5 wt %, often at least about 1 wt %, frequently at least about 2 wt %, at in some embodiments at least about 3 wt %, based on total weight of the composition.

Free-radical initiators contemplated for use in the practice of the present invention typically decompose (i.e., have a half life in the range of about 10 hours) at temperatures in the range of about 70° C. up to 180° C. Exemplary free radical initiators contemplated for use in the practice of the present invention include peroxides (e.g. dicumyl peroxide, dibenzoyl peroxide, 2-butanone peroxide, tert-butyl perbenzoate, di-tert-butyl peroxide, 2,5-bis(tert-butylperoxy)-2,5-dimethylhexane, bis(tert-butyl peroxyisopropyl)benzene, and tert-butyl hydroperoxide), azo compounds (e.g., 2,2'-azobis(2-methyl-propanenitrile), 2,2'-azobis(2-methylbutanenitrile), and 1,1'-azobis(cyclohexanecarbonitrile)). Other free-radical initiators that will be well-known in the art may also be suitable for use in the compositions of the present invention.

Photoinitiators. Free radical initiators also include photoinitiators. For invention compositions that contain a photoinitiator, the curing process can be initiated, for example, by UV radiation. In one embodiment, the photoinitiator is present at a concentration of 0.1 wt % to 5 wt %, based on the total weight of the organic compounds in the composition (excluding any filler). In one embodiment, the photoinitiator comprises 0.5 wt % to 3.0 wt %, based on the total weight of the organic compounds in the composition. In other embodiments, the photoinitiator is present at least about 0.5 wt %, often at least about 1 wt %, frequently at least about 2 wt %, and in some embodiments at least about 3 wt %, based on the total weight of the organic compounds in the composition. Photoinitiators include benzoin derivatives, benzilketals, α,α-dialkoxyacetophenones, α-hydroxyalkylphenones, α-aminoalkylphenones, acylphosphine oxides, titanocene compounds, combinations of benzophenones and amines or Michler's ketone, and the like.

In some embodiments, both photoinitiation and thermal initiation may be desirable. For example, curing of a photoinitiator-containing adhesive can be started by UV irradiation, and in a later processing step, curing can be completed by the application of heat to accomplish a free-radical cure. Both UV and thermal initiators may therefore be added to the adhesive compositions of the invention.

Anionic Catalysts. In other embodiments the initiator is an anionic catalyst. Examples of anionic initiators include Lewis bases such as tertiary amines and imidazoles. Specific examples include benzyldimethlamine, triethylamine, tripropylamine, pyridine, dimethylaminopyridine, dimethylethanolamine, diethylethanolamine, tributylamine, 2-methylimidazole, 2-undecylimidazole, 1-benzyl-2-methylimidazole, 1-cyanoethyl-2-methylimidazole, 1-cyanoethyl-2-phenylimidazole, 1-cyanoethyl-2-undecylimidazole, 1-cyanoethyl-2-ethyl-4-methylimidazole, 1-cyanoethyl-2-isopropylimidazole, 1-cyanoethyl-2-methylimidazole-trimellitate, 1-cyanoethyl-2-phenylimidazole-trimellitate, 1-cyanoethyl-2-ethyl-4-methylimidazole-trimellitate, 1-cyanoethyl-2-undecylimidazole-trimellitate, 2,4-diamino-6-(2'methylimidazolyl-(1'))ethyl-s-triazine, 2,4-diamino-6-(2'-ethyl-4'-methyl-imidazolyl-(1'))ethyl-s-triazine, 2,4-diamino-6-(2'-undecylimidazolyl-(1'))ethyl-s-triazine, 2-phenyl-4-methyl-5-hydroxymethylimidazole, 2-phenyl-4,5-dihydroxymethylimidazole, 1-cyanoethyl-2-phenyl-4,5-di(cyanoethoxymethyl)imidazole, 2-methylimidazole-isocyanuric acid addition compound, 2-phenylimidazole-isocyanuric acid addition compound, 2,4-diamino-6[2'-methylimidazolyl-(1)']ethyl-s-triazine isocyanurate adduct, 4,4'-methylene-bis-(2-ethyl-5-methylimidazole), and the like.

Cationic Catalysts. In other embodiments the initiator is a cationic catalyst. Specific examples include onium compounds. Specific examples include bis[4-(diphenylsulphonio)-phenyl]sulphide bis-hexafluorophosphate, bis[4-(di(2-hydroxyethyl)phenyl)sulphonio-phenyl]sulphide bis-hexafluorophosphate, bis[4-(di(4-(2-hydroxyethyl)phenyl)sulphonio) phenyl]sulphide bis-hexafluoroantimonate, ($\eta^5$-2,4-(cyclopentadienyl)[(1,2,3,4,5,6-$\eta$)-(methylethyl)-benzene]-iron(II) hexafluorophosphate, triarylsulphonium hexafluorophosphate, (tolylcumyl) iodonium tetrakis (pentafluorophenyl) borate, diaryl iodonium hexafluoroantimonate, and the like. In certain embodiments, the invention provides adhesive compositions including 0.5 wt % to about 98 wt % of at least one compound described herein, based on total weight of the composition; optionally, 10 wt % o about 90 wt % of at least one co-monomer selected from acrylates, methacrylates, maleimides, vinyl ethers, vinyl esters, styrenic compounds, allyl functional compounds, and olefins, based on total weight of the composition; 0 to about 90 wt % of a conductive filler; 0.1 wt % to about 5 wt % of at least one curing initiator, based on total weight of the composition; and 0.1 wt % to about 4 wt %, of at least one coupling agent, based on total weight of the composition.

Additional Co-Curing Compounds. In certain aspects, the adhesive compositions of the invention include at least one additional compound that can co-cure with the compound of formula I. The additional compound is typically present in the adhesive compositions from about 10 wt % to about 90 wt % based on total weight of the composition. In such aspects, the composition will typically contain an amount of the co-curing compound equal to at least about 20 wt %, often at least about 30 wt %, frequently at least about 40 wt %, and in some embodiments at least about 50 wt % based on the total weight of the composition. Such compounds include, for example, epoxies (e.g. epoxies based on glydicyl ethers of alcohols, phenols, bisphenols, oligomeric phenolics, phenolic novolacs, cresolic novolacs, acrylates, methacrylates, maleimides, poly-phenol compounds (e.g. poly(4-hydroxystyrene)), anhydrides, dianhydrides, polyanhydrides such as styrene-maleic anhydride co-polymers, imides, carboxylic acids, dithiols, polythiols, phenol functional mono-maleimides, bis-maleimides, polymaleimides, mono-itaconates, mono-maleates, mono-fumarates, acrylic acid, methacrylic acid, cyanate esters, vinyl ethers, vinyl esters, or phenol functional esters, ureas, amides, polyolefins (e.g. amine, carboxylic acid, hydroxy, and epoxy functional) siloxanes (e.g. epoxy, phenolic, carboxylic acid, or thiol functional), cyanoacrylates, allyl functional compounds and styrenic, as well as combinations thereof.

Coupling Agents. In certain aspects, the adhesive compositions of the invention include at least one additional coupling agent. Exemplary coupling agents contemplated for use in the practice of the present invention include silicate esters, metal acrylate salts (e.g., aluminum methacrylate), titanates (e.g., titanium methacryloxyethylacetoacetate triisopropoxide), zirconates, or compounds that contain a copolymerizable group and a chelating ligand (e.g., phosphine, mercaptan, acetoacetate, and the like). In some embodiments, the coupling agent contains both a co-polymerizable function (e.g., vinyl, acrylate, methacrylate, epoxy, thiol, anhydride, isocyanate, and phenol moieties) and a silicate ester function. The silicate ester portion of the coupling agent is capable of condensing with metal hydroxides present on the mineral surface of substrate, while the co-polymerizable function is capable of co-polymerizing with the other reactive components of invention adhesive compositions, such as die-attach pastes. In certain embodiments coupling agents contemplated for use in the practice of the invention are oligomeric silicate coupling agents such as poly(methoxyvinylsiloxane).

Adhesive Paste Compositions Containing

In certain embodiments, the present invention provides adhesive compositions that are of various consistencies including, liquids, gels, pastes and solids. In one embodiment, the adhesive composition is a paste suitable for attaching an electronics die to a substrate (i.e., die-attach pastes). Die attach pastes of the invention are optimized for long-term reliability, rapid inline curing, long pot-life, viscosity and thixotropic control for fast automated dispensing and manufacturing.

In one embodiment, the present invention provides an adhesive composition that include 0.5 wt % to about 98 wt % based on total weight of the composition, of a compound having a structure represented by formula I; 0 to about 90 wt % of a filler, based on total weight of the composition; 0.1 wt % to about 5 wt % of at least one curing initiator, based on total weight of the composition; and 0.1 wt % to about 4 wt %, of at least one coupling agent, based on total weight of the composition.

B-Stageable Adhesives

In certain embodiments, the adhesive compositions and die attach pastes of the invention are b-stageable. As used herein, "B-stageable" refers to the properties of an adhesive having a first solid phase followed by a tacky rubbery stage at elevated temperature, followed by yet another solid phase at an even higher temperature. The transition from the rubbery stage to the second solid phase is thermosetting. However, prior to that, the thermosetting material behaves similarly to a thermoplastic material. Thus, such adhesives allow for low lamination temperatures while providing high thermal stability.

The B-stageable adhesive can be dispensed onto a die or a substrate by a variety of methods well known to those skilled in the art. In some embodiments, the adhesive is cast from solution using techniques such as spin coating, spray coating, stencil printing, screen printing, and the like. This dual stage cure is especially attractive for applications were it is desirable to apply an adhesive in liquid form, cure the material to a non-tacky thermoplastic state, and then cure this B-staged adhesive in a final heating step to bond two or more parts together. Thus, this dual stage cure method of the invention is particularly advantageous for silicon wafer back coatings. The original adhesive mixture can be spin coated onto the back of a silicon wafer. The coating can then be B-staged with heat or light. The coated wafers can then be diced to yield individual microelectronic components, which may be thermally attached directly to a substrate, and/or stacked together. The thermal "tacking step" re-liquifies the adhesive coating and provides a thermoplastic bond between the parts. The final bonding step involves a thermal (or in some cases light-based) cure to cross-link the B-staged adhesive composition. This method of assembly is highly desirable because it is easier to manufacture (especially for stacked die) than a traditional liquid adhesive assembly, and is much less expensive and wasteful compared to film-based adhesive technology.

In certain embodiments, a solvent may be employed in the practice of the invention. For example, when the B-stageable adhesive is spin-coated onto a circular wafer, it is desirable to have an even coating throughout the entire wafer, i.e., the solvent or solvent system should have the ability to deliver the same amount of adhesive to each point on the wafer. Thus, the adhesive will be evenly coated throughout, i.e., there will be the same amount of material at the center of the wafer as at the edges. Ideally, the adhesive is "Newtonian", with a thixotropic slope of 1.0. In certain embodiments, the solvent or solvent systems used to dispense the B-stageable adhesive have slopes ranging from 1.0 to about 1.2.

In some instances, the B-stageable adhesive is dispensed onto the backside of a die that has been coated with a polyimide. Thus, the solvent or solvent system used to dispense the B-stageable adhesive should not have any deleterious effects on the polyimide coating. To achieve this goal, in certain embodiments, the solvent system will include a polar solvent in combination with a nonpolar solvent. Typically, the polar solvent is suitable for use with the alkylated and/or epoxified styrenic oligomers and polymers described herein in B-stageable adhesives, and the nonpolar solvent is a non-solvent for the compounds. In addition, the polar solvent typically has a lower boiling point than the non-polar solvent. Without wishing to be to be limited to a particular theory, it is believed that when the adhesive is dispensed and then B-staged, the lower boiling polar solvent escapes first, leaving behind only the nonpolar non-solvent, essentially precipitating the oligomer uniformly and leaving the polyimide film undamaged.

In some embodiments, the solvent or solvent system has a boiling point ranging from about 150° C. up to about 300° C. In some embodiments, the solvent system is a combination of dimethyl phthalate (DMP), NOPAR 13, and terpineol. In other embodiments, the solvent system is a 1:1 (by volume) ratio of terpineol and NOPAR 13.

In general, adhesive compositions such as die-attach pastes and B-stageable adhesive compositions of the invention, will cure within a temperature range of 80-220° C., and curing will be effected within a length of time of less than 1 minute up to about 60 minutes. The B-stageable adhesive composition may be pre-applied onto either a semiconductor die or onto a substrate. As will be understood by those skilled in the art, the time and temperature curing profile for each adhesive composition will vary, and different compositions can be designed to provide the curing profile that will be suited to a particular industrial manufacturing process.

Additional Compounds. In certain embodiments, the compositions of the invention, such as adhesives (including die-attach paste adhesives), may contain modifiers that lend additional flexibility and toughness to the resultant cured adhesive. Such modifiers may be any thermoset or thermoplastic material having a $T_g$ of 50° C. or less, and typically will be a polymeric material characterized by free rotation about the chemical bonds, the presence of ether groups, and the absence of ring structures. Suitable such modifiers include polyacrylates, poly(butadiene), polyTHF (polymerized tetrahydrofuran, also known as poly(1,4-butanediol)), CTBN (carboxy-terminated butadiene-acrylonitrile) rubber, and polypropylene glycol. When present, toughening compounds may be present in an amount up to about 15 percent by weight of a compound according to formula I and any other monomer in the adhesive.

Inhibitors for free-radical cure may also be added to the adhesive compositions and die-attach pastes described herein to extend the useful shelf life. Examples of free-radical inhibitors include hindered phenols such as 2,6-di-tert-butyl-4-methylphenol; 2,6-di-tert-butyl-4-methoxyphenol; tert-butyl hydroquinone; tetrakis(methylene(3,5-di-tert-butyl-4-hydroxyhydrocinnamate))benzene; 2,2'-methylenebis(6-tert-butyl-p-cresol); and 1,3,5-trimethyl-2,4,6-tris(3',5'-di-tert-butyl-4-hydroxybenzyl)benzene. Other useful hydrogen-donating antioxidants such as derivatives of p-phenylenediamine and diphenylamine. It is also well know in the art that hydrogen-donating antioxidants may be synergistically combined with quinones and metal deactivators to make a very efficient inhibitor package. Examples of suitable quinones include benzoquinone, 2-tert butyl-1,4-benzoquinone; 2-phenyl-1,4-benzoquinone; naphthoquinone, and 2,5-dichloro-1,4-benzoquinone. Examples of metal deactivators include N,N'-bis(3,5-di-tert-butyl-4-hydroxyhydrocinnamoyl)hydrazine; oxalyl bis(benzylidenehydrazide); and N-phenyl-N'-(4-toluenesulfonyl)-p-phenylenediamine.

Nitroxyl radical compounds such as TEMPO (2,2,6,6-tetramethyl-1-piperidnyloxy, free radical) are also effective as inhibitors at low concentrations. The total amount of antioxidant plus synergists typically falls in the range of 100 to 2000 ppm relative to the weight of total base resin. Other additives, such as adhesion promoters, in types and amounts known in the art, may also be added.

The adhesive compositions, such as die-attach paste adhesives, described herein will generally perform within the commercially acceptable ranges for die attach adhesives. Commercially acceptable values for die shear for the adhesives on a 80×80 mil$^2$ silicon die are in the range of greater than or equal to 1 kg at room temperature, and greater than or equal to 0.5 kg at 260° C. Acceptable values for warpage for a 500×500 mil$^2$ die are in the range of less than or equal to 70 Nm at room temperature.

Fillers. In some embodiments, fillers are contemplated for use in the practice of the present invention, which can be electrically conductive and/or thermally conductive, and/or fillers which act primarily to modify the rheology of the resulting composition. Examples of suitable electrically conductive fillers that can be employed in the practice of the present invention include silver, nickel, copper, aluminum, palladium, gold, graphite, metal-coated graphite (e.g., nickel-coated graphite, copper-coated graphite, and the like), and the like. Examples of suitable thermally conductive fillers that can be employed in the practice of the present invention include graphite, aluminum nitride, silicon carbide, boron nitride, diamond dust, zinc oxide, alumina, and the like. Compounds which act primarily to modify rheology include polysiloxanes (such as polydimethyl siloxanes), silica, fumed silica, fumed alumina, fumed titanium dioxide, calcium carbonate and the like.

Underfill Compositions

During its normal service life, an electronic assembly is subjected to repeated cycles of widely varying temperature. Due to the differences in the coefficient of thermal expansion between the electronic component, the solder, and the substrate, thermal cycling can stress the components of the assembly and cause it to fail. To prevent the failure, the gap between the component and the substrate is filled with an underfill material to reinforce the solder material and to absorb some of the stress of the thermal cycling.

In practice, the underfill material is typically dispensed into the gap between and electronic component (such as a flip-chip) and the substrate by injecting the underfill along two or more sides of the component, with the underfill material flowing, usually by capillary action, to fill the gap. Alternatively, underfilling can be accomplished by backfilling the gap between the electronic component and the substrate through a hole in the substrate beneath the chip. In either method, the underfill material must be sufficiently fluid to permit filling very small gaps.

The requirements and preferences for underfills are well known in the art. Specifically, monomers for use in underfills should have high $T_g$ and low $\alpha_1$ CTE, important properties. A high $T_g$, preferably in the range of at least about 100-135° C., and a low modulus or $\alpha_1$, preferably lower than about 60-65 ppm/° C., are optimal for underfill compositions.

The compounds of the invention are particularly suited as monomers or co-monomers in underfill composition. Thus, the present invention provides underfill compositions including at least one compound according to formula I. Optionally, the underfill will also contain a fluxing agent and/or a filler.

Two prominent uses for underfill technology are in packages known in the industry as flip-chip, in which a chip is attached to a lead frame, and ball grid array, in which a package of one or more chips is attached to a printed wire board.

The underfill encapsulation may take place after the reflow of the metallic or polymeric interconnect, or it may take place simultaneously with the reflow. If underfill encapsulation takes place after reflow of the interconnect, a measured amount of underfill encapsulant material will be dispensed along one or more peripheral sides of the electronic assembly and capillary action within the component-to-substrate gap draws the material inward. The substrate may be preheated if needed to achieve the desired level of encapsulant viscosity for the optimum capillary action. After the gap is filled, additional underfill encapsulant may be dispensed along the complete assembly periphery to help reduce stress concentrations and prolong the fatigue life of the assembled structure. The underfill encapsulant is subsequently cured to reach its optimized final properties.

If underfill encapsulation is to take place simultaneously with reflow of the solder or polymeric interconnects, the underfill encapsulant, which can include a fluxing agent if solder is the interconnect material, first is applied to either the substrate or the component; then terminals on the component and substrate are aligned and contacted and the assembly heated to reflow the metallic or polymeric interconnect material. During this heating process, curing of the underfill encapsulant occurs simultaneously with reflow of the metallic or polymeric interconnect material.

A wide variety of acids are contemplated for use as the acidic fluxing agent. Typically, the acidic fluxing agent is a carboxylic acid such as, for example, 3-cyclohexene-1-carboxylic acid, 2-hexeneoic acid, 3-hexeneoic acid, 4-hexeneoic acid, acrylic acid, methacrylic acid, crotonic acid, vinyl acetic acid, tiglic acid, 3,3-dimethylacrylic acid, trans-2-pentenoic acid, 4-pentenoic acid, trans-2-methyl-2-pentenoic acid, 2,2-dimethyl-4-pentenoic acid, trans-2-hexenoic acid, trans-3-hexenoic acid, 2-ethyl-2-hexenoic acid, 6-heptenoic acid, 2-octenoic acid, (+/−)-citronellic acid, (R)-(+)-citronellic acid, (S)-(−)-citronellic acid, undecylenic acid, myristolic acid, palmitoleic acid, oleic acid, elaidic acid, cis-11-eicosenoic acid, erucic acid, nervonic acid, cis-3-chloroacrylic acid, trans-3-chloroacrylic acid, 2-bromoacrylic acid, 2-(trifluoromethyl)acrylic acid, 2-(bromomethyl)acrylic acid, 2-cyclopentene-1-acetic acid, (1R-trans)-2-(bromomethyl)-2-methyl-3-methylenecyclopentaneacetic acid, 2-acetamidoacrylic acid, 5-norbornene-2-carboxylic acid, 3-(phenylthio)acrylic acid, trans-styrylacetic acid, trans-cinnamic acid, alpha-methylcinnamic acid, alpha-phenylcinnamic acid, 2-(trifluoromethyl)cinnamic acid, 2-chlorocinnamic acid, 2-methoxycinnamic acid, cis-2-methoxycinnamic acid, 3-methoxycinnamic acid, 4-methylcinnamic acid, 4-methoxycinnamic acid, 2,5-dimethoxycinnamic acid, 3,4-(methylenedioxy)cinnamic acid, 2,4,5-trimethoxycinnamic acid, 3-methylindene-2-carboxylic acid, and trans-3-(4-methylbenzoyl)acrylic acid, oxalic acid, malonic acid, methylmalonic acid, ethylmalonic acid, butylmalonic acid, dimethylmalonic acid, diethylmalonic acid, succinic acid, methylsuccinic acid, 2,2-dimethylsuccinic acid, 2-ethyl-2-methylsuccinic acid, 2,3-dimethylsuccinic acid, meso-2,3-dimethylsuccinic acid, glutaric acid, (+/−)-2-methylglutaric acid, 3-methylglutaric acid, 2,2-dimethylglutaric acid, 2,4-dimethylglutaric acid, 3,3-dimethylglutaric acid, adipic acid, 3-methyladipic acid, (R)-(+)-3-methyladipic acid, 2,2,5,5-tetramethylhexanedioic acid, pimelic acid, suberic acid, azelaic acid, 1,10-decanedicarboxylic acid, sebacic acid, 1,11-undecanedicarboxylic acid, undecanedioic acid, 1,12-dodecanedicarboxylic acid, hexadecanedioic acid, docosanedioic acid, tetracosanedioic acid, tricarballylic acid, beta-methyltricarballylic acid, 1,2,3,4-butanetetracarboxylic acid, itaconic acid, maleic acid, fumaric acid, citraconic acid, mesaconic acid, trans-glutatonic acid, trans-beta-hydromuconic acid, trans-traumatic acid, trans, trans-muconic acid, cis-aconitic acid, trans aconitic acid, (+/−)-chlorosuccinic acid, (+/−)-bromosuccinic acid, meso-2,3-dibromosuccinic acid, hexa fluoroglutaric acid, perfluoroadipic acid hydrate, dibromo-maleic acid, DL-malic acid, D-malic acid, L-malic acid, (R)-(−)-citramalic acid, (S)-(+)-citramalic acid, (+/−)-2-isopropylmalic acid, 3-hydroxy-3-methylglutaric acid, ketomalonic acid monohydrate, DL-tartaric acid, L-tartaric acid, D-tartaric acid, mucic acid, citric acid, citric acid monohydrate, dihydroflumaric acid hydrate, tetrahydrofuran-2,3,4,5-tetracarboxylic acid, mercaptosuccinic acid, meso-2,3-dimercaptosuccinic acid, thiodiglycolic acid, 3,3'-thiodipropionic acid, 3,3'-dithiodipropionic acid, 3-carboxypropyl disulfide, (+/−)-2-(carboxymethylthio) succinic acid, 2,2',2'',2'''-[1,2-ethanediylidenetetrakis(thio)]-tetrakisacetic acid, nitromethanetrispropionic acid, oxalacetic acid, 2-ketoglutaric acid, 2-oxoadipic acid hydrate, 1,3-acetonedicarboxylic acid, 3-oxoadipic acid, 4-ketopimelic acid, 5-oxoazelaic acid, chelidonic acid, 1,1-cyclopropanedicarboxylic acid, 1,1-cyclobutanedicarboxylic acid, (+/−)-trans-1,2-cyclobutanedicarboxylic acid, trans-DL-1,2-cyclopentanedicarboxylic acid, 3,3-tetramethyleneglutaric acid, (1R.3S)-(+)-camphoric acid, (1S.3R)-(−)-camphoric acid, (+/−)-cyclohexylsuccinic acid, 1,1-cyclohexanediacetic acid, (+/−)-trans-1,2-cyclohexanedicarboxylic acid, (+/−)-1,3-cyclohexanedicarboxylic acid, trans-1,2-cyclohexanedicarboxylic acid, 1,4-cyclohexanedicarboxylic acid, 1,3-adamantanedicarboxylic acid, 3-methylenecyclopropane-trans-1,2-dicarboxylic acid, cis-5-norbornene-endo-2,3-dicarboxylic acid, 1,3,5-cyclohexanetricarboxylic acid, 1,3,5-cyclohexanetricarboxylic acid, kemp's triacid, (1alpha.3alpha.5beta)-1,3,5-trimethyl-1,3,5-cyclohexanetricarboxylic acid, 1,2,3,4-cyclobutane-tetracarboxylic acid, and 1,2,3,4,5,6-cyclo-hexanehexacarboxylic acid monohydrate, phenylmalonic acid, benzylmalonic acid, phenylsuccinic acid, 3-phenylglutaric acid, 1,2-phenylenediacetic acid, homophthalic acid, 1,3-phenylenediacetic acid, 4-carboxyphenoxyacetic acid, 1,4-phenylenediacetic acid, 2,5-dihydroxy-1,4-benzenediacetic acid, 1,4-phenylenediacrylic acid, phthalic acid, isophthalic acid, 1,2,3-benzenetricarboxylic acid hydrate, terephthalic acid, 1,2,4-benzenetricarboxylic acid, 1,2,4,5-benzenetetracarboxylic acid, mellitic acid, 3-(carboxymethylaminomethyl)-4-hydroxybenzoic acid, 4-methylphthalic acid, 2-bromoterephthalic acid, 4-bromoisophthalic acid, 4-hydroxyisophthalic acid, 4-nitrophthalic acid, nitrophthalic acid, 1,4-phenylenedipropionic acid, 5-tert-butylisophthalic acid, 5-hydroxyisophthalic acid, 5-nitroisophthalic acid, 5-(4-carboxy-2-nitrophenoxy)- isophthalic acid, diphenic acid, 4,4"-biphenyldicarboxylic acid, 5,5"dithiobis(2-nitrobenzoic acid), 4-[4-(2-carboxybenozoyl)phenyl]-butyric acid, pamoic acid, 1,4-naphthalenedicarboxylic acid, 2,3-naphthalenedicarboxylic acid, 2,6-naphthalenedicarboxylic acid, 1,4,5,8-naphthalene-tetracarboxylic acid hydrate, 2,7-di-tert-butyl-9,9-dimethyl-4,5-xanthenedicarboxylic acid, and the like.

A particularly useful carboxylic acid for the preparation of the latent fluxing agents of the present invention is DIACID 1550®, a monocyclic $C_{21}$ dicarboxylic acid product derived from tall oil fatty acids, commercially available from Westvaco Corporation.

Mold Compounds and Compositions

In the electronics industry, a semiconductor chip or die mounted to a "package" substrate may be overmolded with a mold compound to provide a level of protection from environmental effects such as moisture and contaminants.

In terms of reliability performance, various properties of mold compositions materials are generally considered important. The properties desirable for mold compositions are known in the art. See, for example, U.S. Pat. Nos. 7,294,915, 6,512,031, and 6,429,238. These include low CTE, low modulus, adhesion, and high fracture toughness of the cured resin. A high $T_g$, preferably in the range of at least about 100-135° C., and a low modulus or $\alpha_1$, preferably lower than about 60-65 ppm/° C., are optimal for mold compositions. See, for example, U.S. Pat. Nos. 6,512,031 and 5,834,848. A typical overmolding process places a solid or semi-solid molding compound over the chip using a mold press. The package is then transferred through a heated mold that causes the molding compound to flow and encapsulate the chip.

Mold compositions are highly filled compositions. They are typically filled with silica. This high filler loading is critical to their performance in terms of CTE (coefficient of thermal expansion), flame retardance, and thermal conductivity.

The compounds of the present invention were found to have properties desirable of mold compounds. Specifically, the compounds of formula I of the invention have a high $T_g$ and low $\alpha_1$, CTE. A high $T_g$, preferably in the range of at least about 100-135° C., and a low modulus or $\alpha_1$, preferably lower than about 60-65 ppm/° C., are optimal for mold compositions. Thus, the present invention provides mold compositions containing at least one compound according to formula I.

Assemblies

The present invention also provides assemblies of components adhered together by the above-described adhesive compositions (e.g., B-stageable adhesives and die-attach pastes) of the invention. Thus, for example, assemblies comprising a first article adhered to a second article by a cured aliquot of an adhesive composition containing at least one compound of formula I are provided. Articles contemplated for assembly employing invention compositions include electronic components such as dies, memory devices (e.g. as flash memory devices), ASIC devices, microprocessors, and other microelectronic components. Assemblies also include microelectronic devices, such as copper lead frames, Alloy 42 lead frames, silicon dice, gallium arsenide dice, and germanium dice, that are adhered to a substrate by a cured aliquot of the above-described adhesive compositions Additional embodiments of the invention include adhesively bonded structures containing at least one functionalized styrene compound described herein. Non-limiting examples of the adhesively bonded structures include electronic components bonded to a substrate, and circuit components bonded to printed wire boards. In other embodiments of the invention, articles of manufactures can be comprised substantially of a cured amount of the composition described herein, such as an industrial, marine, automotive, airline, aerospace, sporting goods, medical or dental article. Such articles of manufacture can also include fillers, extenders, pigments and/or reinforcing materials along with the compositions disclosed herein.

Conditions suitable to cure invention die attach paste adhesives include subjecting the above-described assembly to a temperature of less than about 200° C. for about 0.5 up to 2 minutes. This rapid, short duration heating can be accomplished in a variety of ways, e.g., with an in-line heated rail, a belt furnace, or the like. Optionally, the material can be oven cured at 150-220°C.

Methods of Using Functionalized Styrene Compounds and Adhesive Compositions

According to the present invention, methods for adhesively attaching a first article to a second article are provided. Such methods can be performed, for example, by a) applying an adhesive composition of the invention to the first article, the second article or both the first and second articles; b) contacting the first article and the second article, where the first article and the second article are separated only by the adhesive composition applied in step a); and c) curing the adhesive composition applied in step a), thereby adhesively attaching the first article to the second article.

In one aspect of this method, the first and second articles are a semiconductor die and a substrate, respectively. Typically, according to this aspect the adhesive is a die attach paste. The method can include the steps of applying the adhesive composition (e.g. die attach paste) to the substrate, the semiconductor die, or both the substrate and the semiconductor die; b) melting the adhesive composition applied in step a); c) contacting the semiconductor device and the substrate, where the die and substrate are separated only by the adhesive composition applied in step a); and d) curing the adhesive composition applied in step a), thereby adhesively attaching the semiconductor device to the substrate. Applying the adhesive composition can include spin-coating, spray coating, stencil printing, screen printing and other methods well known in the art.

It will be understood those of skill in the art that using the compounds and methods of the present invention, it is possible to prepare adhesives having a wide range of cross-link density by the judicious choice and amount of a compound having a structure represented by formula I. The greater proportion of polyfunctional compounds reacted, the greater the cross-link density. If thermoplastic properties are desired, the adhesive compositions can be prepared from (or at least contain a higher percentage of) mono-functional compounds to limit the cross-link density. A minor amount of poly-functional compounds can be added to provide some cross-linking and strength to the composition, provided the amount of poly-functional compounds is limited to an amount that does not diminish the desired thermoplastic properties. Within these parameters, the strength and elasticity of individual adhesives can be tailored to a particular end-use application.

In still further embodiments, the invention provides B-stageable type methods for adhesively attaching a semiconductor die to a substrate. Such methods can be performed, for example, by applying an invention adhesive composition to the substrate, the semiconductor device or both the substrate and the semiconductor device; melting the applied adhesive composition applied; (c) contacting the semiconductor device and the substrate, such that the die and substrate are separated only by the applied adhesive composition; and curing the applied adhesive composition, thereby attaching the semiconductor device to the substrate.

Properties of Adhesives Containing Functionalized Styrene Compounds

Advantageously, the functionalized styrene compounds of formula I can impart many properties that are desirable in an adhesive. Historically, the large majority of integrated circuits have been mounted on printed circuit boards using lead-based soldering. However, the demand for lead-free materials is increasing year by year, and electrically conductive adhesives are seen as an environmentally-friendly alternative.

Adhesiveness. To fully replace lead-based solders, adhesives in the microelectronic industry, adhesives must address the need for signal and power distribution, heat dissipation (i.e., cooling) while at the same time having and maintaining high adhesiveness. Conductive adhesives, for example, typically have conductive fillers dispersed in a polymer matrix. The polymer matrix, when cured, provides the mechanical adhesion, but can interfere with conductivity and increase electrical resistance.

Compounds of the present invention impart increases adhesivenesss to polymer compositions. When added to a BMI-containing adhesive compositions, an allylated liquid styrene oligomer of the invention increased adhesiveness by nearly two-fold over the same composition containing only BMI, as described in EXAMPLE 5, below.

Thus the present invention provides methods for increasing the adhesiveness of an adhesive composition by replacing all or a portion of a monomer (such as a bismaleimide monomer) in the composition, with a functionalized styrene compound of the invention. In one embodiment, the compound can be represented by structural formula I. In other embodiments the compound has the structure represented by formulae II-V.

The invention will now be described by the following illustrative, non-limiting examples.

EXAMPLES

Example 1

Allylation of Pure Styrene Oligomer

A screening test was run for the allylation of a styrene oligomer. A 15 ml flask was charged with 1.0 g Piccolastic™ A75 (low molecular weight pure styrene hydrocarbon resin from Eastman Chemical Co., Kingsport, Tenn.), 1.0 g allyl chloride, 5.0 g nitroethane and 0.1 g zinc chloride. This mixture was magnetically stirred at room temperature for five days. The volatiles were removed on a rotary evaporator and the residue was dissolved into 15 ml acetone. The acetone solution was then dripped into flask containing 150 ml of methanol which was stirred vigorously throughout the addition. A buff colored solid was recovered via filtration followed by methanol rinses. The product was dried and a TGA was run on the solid. This product had a decomposition onset of 390° C. (the Piccolastic™ starting material onset was 295° C.). The test material also had a char yield of 24 weight percent at 500° C., while the Piccolastic™ A-75 starting compound had less than 1% residual weight at 500° C. An FTIR was run on the product, which revealed new absorptions at 1637, 993, and 910 wavenumbers versus the Piccolastic™ starting material. All of this was consistent with the successful allylation of the styrene oligomer.

Example 2

Allylation of Liquid Styrene Oligomer

A 125 ml flask was charged with 10.44 g (0.1 equivalent) Piccolastic™ A5 (a liquid styrene oligomer from Eastman), 5.8 g (0.1 mole) allyl alcohol, and 14.4 g (0.106 mole) zinc chloride. This mixture was stirred and heated in an oil bath at 100° C. for three hours. The mixture turned to a black tarry mass in the flask. The residue was extracted with three 100 ml portions of toluene. The toluene extract was then rinsed with water, dried and then evaporated to give 10.8 g of a viscous amber liquid. A differential scanning calorimetry measurement (DSC) was performed on this product in the presence of 2% added dicumyl peroxide. An exotherm was observed with an onset of 154.6° C. and a maxima at 184.2° C. The cure energy was 26.5 joules per gram. Fourier transform infrared spectroscopy (FTIR) of this product again revealed the same characteristic absorptions (1637, 993, and 910 wavenumbers) apparent in the previous example.

Example 3

Alternative Allylation of Liquid Styrene Oligomer

A 500 ml flask was charged with 10.4 g (0.1 equivalent) Piccolastic A5, 15.42 g (0.113 mole) zinc chloride, and a magnetic stir bar. The flask was stirred and heated to 140° C. and then 8.7 g (0.15 mole) allyl alcohol was dripped in over a one hour period. Heating was continued for another half hour and then the flask was cooled. The residue was extracted with four 50 ml portions of toluene. The combined extracts were passed over 35 g silica gel followed by another 100 ml of fresh toluene. The toluene was then removed on a rotary evaporator under vacuum and the residue was sparged with argon at 70° C. to yield 11.82 g of a viscous, light amber liquid. This product appeared to be substantially equivalent (via FTIR, and TGA) to the product from EXAMPLE 2).

Example 4

Reaction of Allyl Styrene Oligomer with Bismaleimide

One part by weight of the product from EXAMPLE 3 was mixed with two parts by weight of the bismaleimide of dimer diamine. A sample of this un-catalyzed mix was heated in a DSC and was found to have two exotherms. The first exotherm had a maxima at 188.8° C. and had a cure energy of 26.6 joules per gram. The second cure had a maxima at 281.5° C. It is believed that the first exotherm resulted from an ene-reaction between the allylated styrene oligomer and the maleimide functions of the BMI. The second cure event is believed to be from Diels-Alder type reactions of the maleimide residues and the ene addition product. A TGA on the un-catalyzed mix showed 88.5 residual weight at 400° C., and a decomposition onset of 420° C.

Example 5

Adhesiveness of Allylated Polystyrene

Testing was done on 2:1 (weight to weight) mixture of the dimer diamine BMI ("X-BMI", prepared as described in the U.S. Pat. No. 5,973,166, the entire disclosure of which is incorporated herein by reference. X-BMI is a product which is described in U.S. Pat. No. 5,973,166, EXAMPLE 6, the fourth product in Table 1. As can be understood from the description provided in U.S. Pat. No. 5,973,166, X-BMI is a bismaleimide of Versamine® 552, prepared by using methanesulfonic acid and triethylamine) added to the allylated polystyrene from EXAMPLE 3. This mixture was catalyzed with 2% dicumyl peroxide. Two controls were used. The first of these was the X-BMI by itself, catalyzed with 2% dicumyl peroxide. The second control was a 2:1 mix of the BMI:Piccolastic™ A5, catalyzed in the same way. These mixtures were used to bond aluminum (0.177 inch diameter) studs to freshly cleaned copper slugs. Room temperature adhesion data was generated for these samples using a Sebastian III tensile tester. The results of those tests are summarized in Table 1.

TABLE 1

Tensile Adhesion for BMI + Allylated Styrene Oligomers

| 2:1 X-BMI:Example 3 (cured 0.5 hr @ 200° C.) | | 2:1 X-BMI:Example 3 (cured 1.0 hr @ 200° C.) | | 2:1 X-BMI:Piccolastic ™ A5 (cured 1.0 hr @ 200° C.) | | X-BMI Control (cured 1.0 hr @ 200° C.) | |
|---|---|---|---|---|---|---|---|
| Part | Adhesion (lbs. force) | Part | Adhesion (lbs. force) | Part | Adhesion (lbs. force) | Part | Adhesion (lbs. force) |
| 1 | 54 | 1 | 51 | 1 | 42 | 1 | 23 |
| 2 | 32 | 2 | 76 | 2 | 46 | 2 | 29 |
| 3 | 50 | 3 | 99 | 3 | 22 | 3 | 7 |
| 4 | 43 | 4 | 42 | 4 | 36 | 4 | 24 |
| 5 | 35 | 5 | 86 | 5 | 37 | 5 | 21 |
| 6 | 38 | 6 | 76 | 6 | 55 | 6 | 21 |
| 7 | 52 | 7 | 63 | 7 | 57 | 7 | 25 |
| 8 | 38 | 8 | 42 | 8 | 33 | 8 | 13 |
| 9 | 54 | 9 | 66 | 9 | 9 | 9 | 18 |
| 10 | 75 | 10 | 56 | 10 | 18 | 10 | 18 |
| Average = 47.1 lbs | | Average = 65.7 lbs. | | Average = 34.9 lbs. | | Average = 19.9 lbs. | |
| Std. dev. = 12.7 lbs | | Std. dev. = 18.8 lbs. | | Std. dev. = 14.8 lbs. | | Std. dev. = 6.3 lbs | |

The tensile adhesion data from Table 1 demonstrates an adhesion enhancement via the addition of the allylated styrene oligomer from EXAMPLE 3 to the X-BMI monomer. Addition of the non-functionalized Piccolastic™ resulted in a 75% increase in adhesion versus the X-BMI-only control after a one hour cure, while the mix containing the EXAMPLE 3 compound had a 230% increase under the same conditions. A shorter (half hour) cure using the EXAMPLE 3 compound gave a 137% increase in adhesion, while the X-BMI control often parts (results not shown) had an average adhesion of 19.3 pounds force under the same conditions. This latter result suggests that mixtures containing the compound from EXAMPLE 3 continued to improve in adhesion with continued heating, while the X-BMI-only control did not.

Example 6

Simultaneous Co-Polymerization and Allylation of Liquid Styrene Oligomer

A 25 ml flask was charged with 1.56 g (0.015 equivalent) Piccolastic™ A5, 0.68 g (0.005 equivalent) allyl maleimide, 2.88 g (0.021 equivalent) zinc chloride and 2.0 g chlorobenzene. This mixture was magnetically stirred in an oil bath set at 75° C. for eight hours. The mixture was then precipitated into 100 ml of methanol. The residue weighed 0.58 g after drying. The material was a viscous, sticky liquid. An FTIR was run on this compound and it revealed new absorptions at 1713 and 828 wavenumbers (which was consistent with the incorporation of maleimide functionality).

While this invention has been described with respect to these specific examples, it should be clear that other modifications and variations would be possible without departing from the spirit of this invention.

What is claimed is:

1. A compound having the structure of formula I:

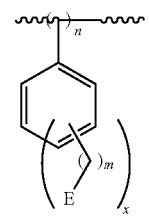

wherein:
  E is a moiety selected from the group consisting of maleimido, acrylate, methacrylate, allyl, methallyl, epoxy, oxetane, a partially or fully epoxidized allyl, and a partially or fully epoxidized methallyl;
  n is an integer having the value between 3 and about 100;

m is an integer having the value between 0 and 12; and x is an integer having the value between 1 and 5.

2. The compound of claim 1, wherein E is selected from the group consisting of allyl, methallyl, epoxy, acrylate, and methacrylate.

3. The compound of claim 1, wherein E is selected from the group consisting of allyl, partially or fully epoxidized allyl, methallyl and partially or fully epoxidized methallyl.

4. The compound of claim 1, selected from the group consisting of Compounds 1-6:

Compound 1

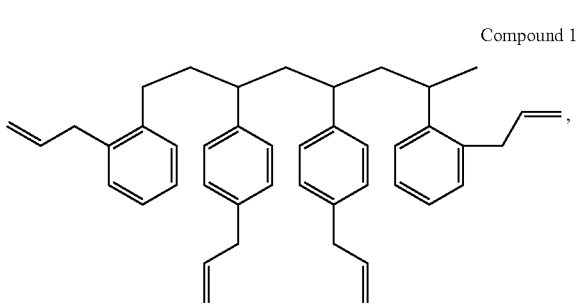

Compound 2

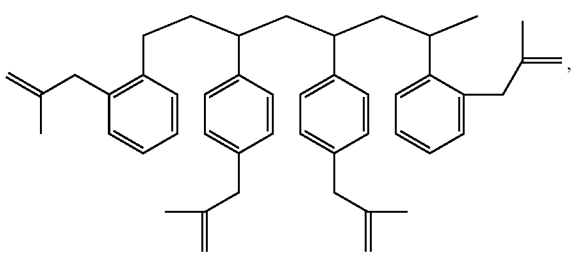

Compound 3

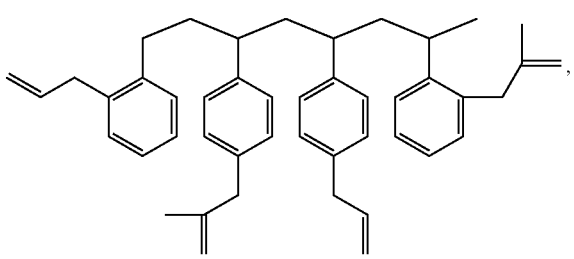

Compound 4

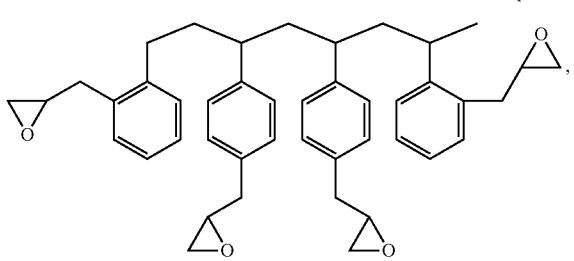

Compound 5

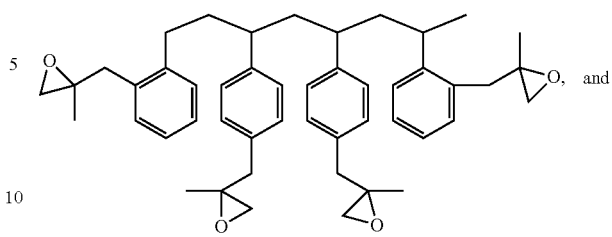

and

Compound 6

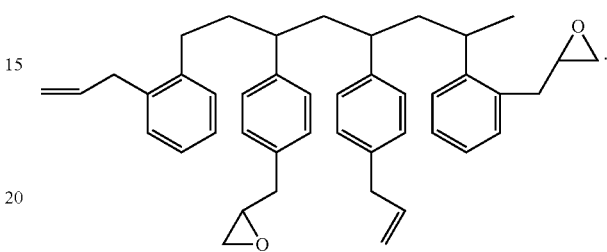

5. A composition comprising a compound of claim 1.

6. The composition of claim 5, wherein the composition is an adhesive.

7. The composition of claim 6, wherein the composition is B-stageable.

8. The compositions of claim 5, wherein the adhesive is cured.

9. The composition of claim 5, further comprising at least one curing initiator, co-monomer, co-curing compound, coupling agent, or filler.

10. A method for increasing the adhesiveness of a composition comprising a monomer, comprising the step of replacing all or a portion of the monomer in the composition with a compound of claim 1.

11. The method of claim 10, wherein the monomer is a bismaleimide or an acrylate.

12. The method of claim 10, wherein replacing all or a portion of the monomer in the composition increases the adhesiveness of the composition by at least about 100%.

13. A method for synthesizing a compound of claim 1, comprising alkylating an oligomer or polymer obtained by polymerization of styrene with an alkylating agent X-E in the presence of a Lewis acid catalyst wherein:

E is selected from the group consisting of maleimido, acrylate, methacrylate, allyl, methallyl, epoxy, and oxetane; and X is Cl, Br, I, —OH, or α-olefin, thereby obtaining a compound of structure I.

14. The method of claim 13, wherein E is the group consisting of allyl and methallyl.

15. The method of claim 13, further comprising partially or fully oxidizing the allyl or methallyl functional groups to epoxy residues.

16. A compound obtained by the method of claim 13.

* * * * *